(12) United States Patent
Sonmez et al.

(10) Patent No.: US 12,708,369 B2
(45) Date of Patent: Aug. 18, 2026

(54) SYSTEMS AND METHODS FOR TREATING ANEURYSMS

(71) Applicant: Covidien LP, Mansfield, MA (US)

(72) Inventors: Merdim Sonmez, Tustin, CA (US); Junwei Li, Irvine, CA (US); Madeleine Roseen, Irvine, CA (US); Mehdi Rashidi, Irvine, CA (US)

(73) Assignee: Covidien LP, Mansfield, MA (US)

( * ) Notice: Subject to any disclaimer, the term of this patent is extended or adjusted under 35 U.S.C. 154(b) by 334 days.

(21) Appl. No.: 18/176,088

(22) Filed: Feb. 28, 2023

(65) Prior Publication Data

US 2023/0301660 A1 Sep. 28, 2023

Related U.S. Application Data

(60) Provisional application No. 63/269,933, filed on Mar. 25, 2022.

(51) Int. Cl.
*A61B 17/12* (2006.01)
*A61B 17/00* (2006.01)

(52) U.S. Cl.
CPC .... *A61B 17/12113* (2013.01); *A61B 17/1214* (2013.01); *A61B 2017/12063* (2013.01)

(58) Field of Classification Search
CPC .......... A61B 17/12113; A61B 17/1214; A61B 17/12172; A61B 17/12186; A61B 2017/12063; A61B 2017/00004; A61B 17/12022; A61F 2/01; A61F 2/0105; A61F 2/0108; A61F 2/013
See application file for complete search history.

(56) References Cited

U.S. PATENT DOCUMENTS 5,261,916 A 11/1993 Engelson
5,601,600 A 2/1997 Ton
(Continued)

FOREIGN PATENT DOCUMENTS

CA 2167911 A1 * 1/1996
CA 3031482 A1 8/2017
(Continued)

OTHER PUBLICATIONS

"Material Spotlight: Teflon for Electrical Insulation, Oct. 26, 2021, ESPE Manufacturing, p. 2" (Year: 2021).*
(Continued)

*Primary Examiner* — Tan-Uyen T Ho
*Assistant Examiner* — Lindsey R. Rivers
(74) *Attorney, Agent, or Firm* — Fortem IP LLP

(57) ABSTRACT

Treatment of aneurysms can be improved by delivering an occlusive member (e.g., an expandable braid) to an aneurysm sac in conjunction with an embolic element (e.g., coils, embolic material). A treatment system for such treatment can include an electrolytically corrodible conduit having a proximal portion, a distal portion, and a detachment zone between the proximal portion and the distal portion. An occlusive member having a proximal hub is coupled to the conduit distal portion. The conduit has a lumen configured to pass an embolic element therethrough. An inner electrode assembly can be slidably disposed within the conduit lumen to facilitate electrolytic detachment of the occlusive member at the detachment zone.

19 Claims, 18 Drawing Sheets

(56) References Cited

U.S. PATENT DOCUMENTS 5,749,894 A 5/1998 Engelson
5,846,261 A 12/1998 Kotula et al.
5,916,235 A 6/1999 Guglielmi
5,964,797 A 10/1999 Ho
6,077,260 A * 6/2000 Wheelock ........ A61B 17/12022 606/191
6,936,058 B2 8/2005 Forde et al.
7,128,736 B1 10/2006 Abrams et al.
7,367,986 B2 5/2008 Mazzocchi et al.
7,473,266 B2 1/2009 Glaser
7,879,065 B2 2/2011 Gesswein et al.
8,372,062 B2 2/2013 Murphy et al.
8,690,936 B2 4/2014 Nguyen et al.
9,339,275 B2 5/2016 Trommeter et al.
9,681,861 B2 6/2017 Heisel et al.
9,713,475 B2 7/2017 Divino et al.
9,918,718 B2 3/2018 Lorenzo
10,130,372 B2 11/2018 Griffin
10,932,933 B2 3/2021 Bardsley et al.
10,952,740 B2 3/2021 Dasnurkar et al.
11,076,860 B2 8/2021 Lorenzo
11,134,953 B2 10/2021 Solaun
11,179,159 B2 11/2021 Cox et al.
11,504,816 B2 11/2022 Nguyen et al.
11,826,863 B2 11/2023 Li et al.
2001/0000797 A1 5/2001 Mazzocchi
2003/0093097 A1 5/2003 Avellanet et al.
2004/0176798 A1 9/2004 Foy et al.
2004/0236344 A1 11/2004 Monstadt et al.
2005/0038470 A1 2/2005 Van et al.
2005/0119684 A1 6/2005 Guterman et al.
2006/0064151 A1 3/2006 Guterman et al.
2006/0116714 A1 6/2006 Sepetka et al.
2006/0276824 A1 12/2006 Mitelberg et al.
2006/0276829 A1 12/2006 Balgobin et al.
2007/0179520 A1 8/2007 West
2007/0186933 A1 8/2007 Domingo et al.
2007/0198075 A1 8/2007 Levy
2007/0221230 A1 9/2007 Thompson et al.
2007/0299461 A1 12/2007 Elliott
2008/0119886 A1 5/2008 Greenhalgh et al.
2008/0195137 A1 8/2008 Alleyne et al.
2008/0221554 A1 9/2008 OConnor et al.
2008/0221703 A1 9/2008 Que et al.
2008/0281350 A1 11/2008 Sepetka et al.
2008/0283066 A1 11/2008 Delgado et al.
2009/0036877 A1 2/2009 Nardone et al.
2009/0099592 A1 4/2009 Buiser et al.
2009/0287294 A1 11/2009 Rosqueta et al.
2010/0023048 A1 1/2010 Mach
2010/0121350 A1 5/2010 Mirigian
2010/0268251 A1* 10/2010 Chen .................. A61B 17/1215 606/139
2011/0144669 A1 6/2011 Becking et al.
2011/0238041 A1 9/2011 Lim et al.
2011/0282378 A1* 11/2011 Murphy ............. A61B 17/1214 606/195
2012/0123510 A1 5/2012 Liungman
2012/0143301 A1 6/2012 Maslanka et al.
2012/0271344 A1 10/2012 Ford et al.
2013/0066357 A1 3/2013 Aboytes et al.
2013/0073026 A1 3/2013 Russo et al.
2013/0138136 A1 5/2013 Beckham et al.
2013/0211495 A1 8/2013 Halden et al.
2014/0039542 A1 2/2014 Trommeter et al.
2014/0135811 A1 5/2014 Divino et al.
2014/0200607 A1 7/2014 Sepetka et al.
2014/0215792 A1 8/2014 Leopold et al.
2014/0257360 A1 9/2014 Keillor
2014/0257374 A1 9/2014 Heisel et al.
2015/0005808 A1 1/2015 Chouinard et al.
2015/0272589 A1 10/2015 Lorenzo
2015/0313605 A1 11/2015 Griffin
2015/0335333 A1 11/2015 Jones et al.
2015/0343181 A1 12/2015 Bradway et al.
2016/0022445 A1 1/2016 Ruvalcaba et al.
2016/0030050 A1 2/2016 Franano et al.
2016/0106437 A1 4/2016 Van Der Burg et al.
2016/0128699 A1 5/2016 Hadley et al.
2016/0249935 A1 9/2016 Hewitt et al.
2016/0331381 A1 11/2016 Ma
2017/0105739 A1 4/2017 Dias et al.
2017/0156734 A1 6/2017 Griffin
2017/0224350 A1 8/2017 Shimizu et al.
2017/0224355 A1 8/2017 Bowman et al.
2017/0354419 A1 12/2017 Teoh et al.
2017/0354421 A1 12/2017 Maguire et al.
2017/0367704 A1* 12/2017 Rhee ................ A61B 17/12172
2017/0367707 A1 12/2017 Divino
2017/0367713 A1 12/2017 Greene et al.
2018/0070955 A1 3/2018 Greene et al.
2018/0110797 A1 4/2018 Li et al.
2018/0132856 A1 5/2018 Wierzbicki et al.
2018/0140305 A1 5/2018 Connor
2018/0206852 A1 7/2018 Moeller
2018/0242979 A1 8/2018 Lorenzo
2018/0256171 A1 9/2018 Chow et al.
2018/0317932 A1 11/2018 H'Doubler
2019/0008522 A1 1/2019 Lorenzo
2019/0009057 A1 1/2019 Li et al.
2019/0053807 A1 2/2019 Tassoni et al.
2019/0192167 A1 6/2019 Lorenzo
2019/0223876 A1 7/2019 Badruddin et al.
2019/0223881 A1 7/2019 Hewitt et al.
2019/0343532 A1 11/2019 Divino et al.
2019/0351107 A1 11/2019 Sawhney et al.
2020/0113576 A1 4/2020 Gorochow et al.
2020/0138448 A1 5/2020 Dasnurkar et al.
2020/0268392 A1 8/2020 Choi et al.
2020/0315644 A1 10/2020 Bowman
2021/0128160 A1 5/2021 Li et al.
2021/0128161 A1 5/2021 Nageswaran et al.
2021/0128162 A1 5/2021 Rhee et al.
2021/0128165 A1 5/2021 Pulugurtha et al.
2021/0128167 A1 5/2021 Patel et al.
2021/0128168 A1 5/2021 Nguyen et al.
2021/0128169 A1 5/2021 Li et al.
2021/0129275 A1 5/2021 Nguyen et al.
2021/0137530 A1 5/2021 Greene et al.
2021/0153872 A1 5/2021 Nguyen et al.
2021/0161643 A1 6/2021 Totten et al.
2021/0196284 A1 7/2021 Gorochow et al.
2021/0212698 A1 7/2021 Connor
2022/0304696 A2 9/2022 Rhee et al.
2023/0023511 A1 1/2023 Nguyen et al.
2024/0075565 A1 3/2024 Li et al.

FOREIGN PATENT DOCUMENTS

CN 105105812 A 12/2015
EP 2468348 B1 10/2016
WO 9905977 A1 2/1999
WO 03011151 A1 2/2003
WO 2007079402 A2 7/2007
WO WO-2014008460 A2 * 1/2014 ............ A61F 2/966
WO 2015160721 A1 10/2015
WO 2015166013 A1 11/2015
WO 2018050262 A1 3/2018
WO 2019038293 A1 2/2019

OTHER PUBLICATIONS

International Search Report and Written Opinion mailed Feb. 17, 2021, International Application No. PCT/US20/70741, 6 pages.
International Search Report and Written Opinion mailed Feb. 23, 2021, International Application No. PCT/US20/70743, 14 pages.
International Search Report and Written Opinion mailed Apr. 13, 2021, International Application No. PCT/US20/70742, 18 pages.

* cited by examiner

132
W
124
126
122
230
A
130
102
116
134
N
106
108

A
230
136
132
136

102
116
130
134
N
106
108

A
230
136
136

116
132
102
N
106
108

A
102
114
112
N
106
108

102
406
426
434
428
436
432
430
402
400
404

460
462
454
458
450
456
452

SYSTEMS AND METHODS FOR TREATING ANEURYSMS

CROSS-REFERENCE TO RELATED APPLICATION(S)

The present application claims the benefit of priority to U.S. Patent Application No. 63/269,933, filed Mar. 25, 2022, which is incorporated by reference herein in its entirety.

TECHNICAL FIELD

The present technology relates to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The present technology is illustrated, for example, according to various aspects described below. These are provided as examples and do not limit the present technology.

In one aspect of the technology, a treatment system includes a conduit having a proximal portion, a distal portion, and a sidewall, wherein the sidewall defines an electrolytically corrodible detachment zone between the proximal portion and the distal portion. The detachment zone defines one or more apertures formed therein and/or defines a reduced wall thickness relative to non-detachment zone portions of the sidewall so that the detachment zone is configured to cause separation of the proximal portion and the distal portion in response to a flow of an electrical current through the detachment zone. The conduit defines a lumen configured to pass an embolic element therethrough. The treatment system additionally includes an expandable occlusive member comprising a proximal hub coupled to the conduit distal portion. The occlusive member is configured to be positioned at an intrasaccular treatment site. The treatment system also includes an elongate conductive member slidably disposed within the lumen and having a distally located electrode configured to be disposed adjacent the detachment zone.

In another aspect of the technology, a treatment system includes an elongate tubular member having a proximal portion, a distal portion, and a sidewall, wherein the sidewall defines an electrolytically corrodible detachment zone between the proximal portion and the distal portion. The detachment zone defines one or more apertures formed therein and/or defines a reduced wall thickness relative to non-detachment zone portions of the sidewall. The tubular member also includes a lumen extending therethrough. The treatment system further includes a medical device coupled to the tubular member distal portion, and an elongate rod slidably disposed within the tubular member lumen and having a distally located electrode configured to be disposed adjacent the detachment zone.

In another aspect of the present technology, a method includes disposing an occlusive member at a treatment site, the occlusive member coupled to a distal end of a conduit having a sidewall that defines a detachment zone that includes a one or more apertures formed therein and/or a reduced wall thickness relative to non-detachment zone portions of the sidewall. The method further includes expanding the occlusive member at the treatment site, and disposing an elongate conductive member within a lumen of the conduit such that a distally located electrode is positioned adjacent to the detachment zone. The method additionally includes applying a voltage across the conduit and the elongate conductive member, thereby electrolytically severing the conduit at the detachment zone, and then proximally retracting both the conduit and the conductive member while the occlusive member remains within the aneurysm cavity.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

Figure 1A:
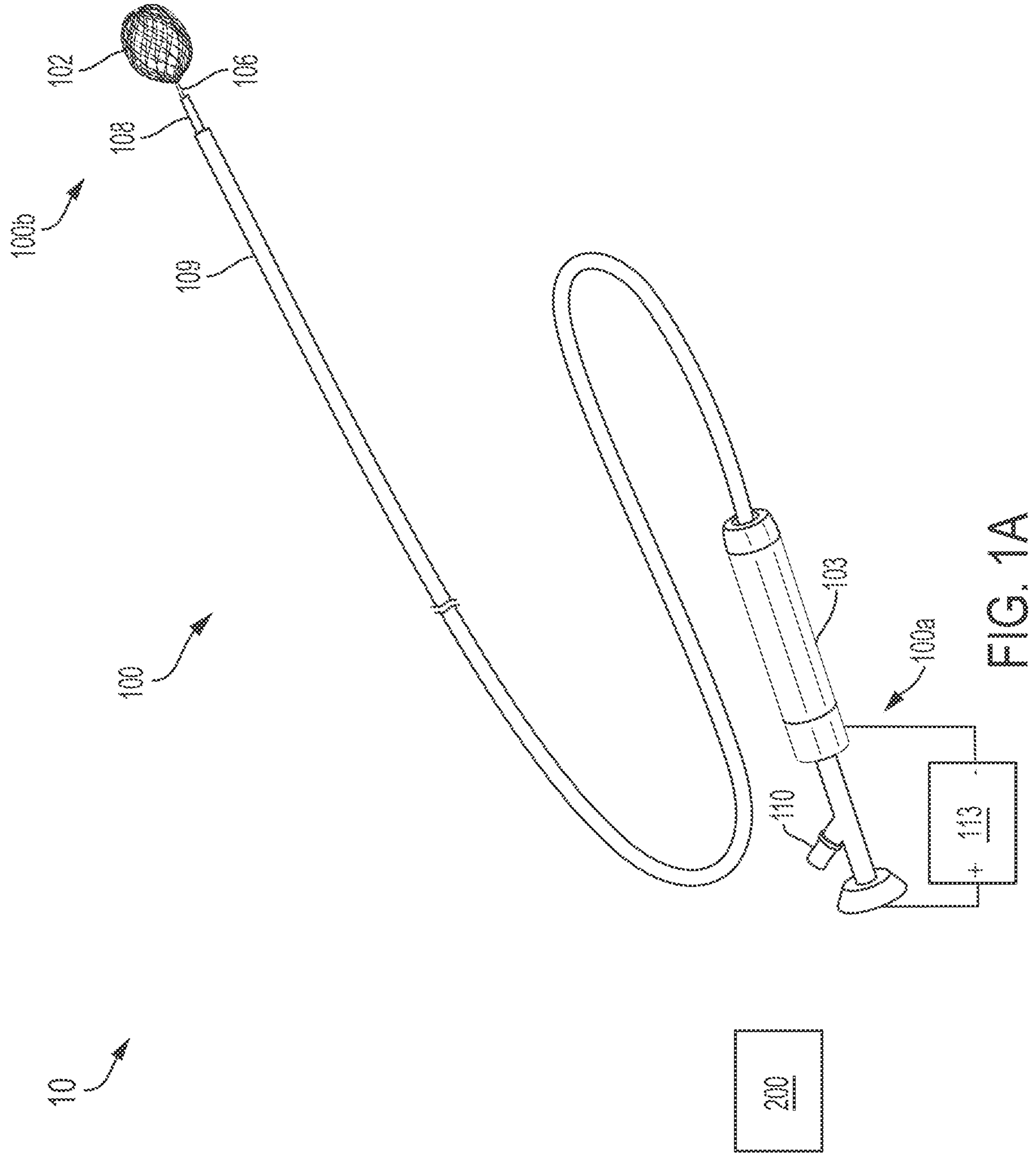
FIG. 1A shows a perspective view of a system for treating an aneurysm in accordance with the present technology.

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Once the occlusive member has deployed within the aneurysm and the embolic element has been delivered, the occlusive member may be detached from the delivery assembly. Suitable detachment mechanisms must be as small as possible so as to be guided through the fine bore of the catheter to the treatment site, while on the other hand they must securely and reliably produce detachment of the intrasaccular implant. Absent a reliable detachment of the intrasaccular implant, withdrawal of the delivery conduit and catheter may cause unintended removal of the occlusive member from the cavity to be occluded and thus injure and/or rupture of the wall of the cavity or vessel. In some embodiments, an electrolytic detachment mechanism as described herein can be used to facilitate reliable, controlled detachment of the occlusive member.

The occlusive member can be implanted in body cavities or blood vessels. In addition to the occlusive member, the treatment system can comprise a voltage source, a cathode, a delivery conduit, and a catheter. The occlusive member and the delivery conduit can be coupled together such that both can be slid in the catheter in the longitudinal direction. For example, the occlusive member can be coupled to a distal portion of the conduit, and the conduit can include a detachment zone configured to be electrolytically severed. In some embodiments, the conduit can be adapted to serve as an anode, such that a portion of the conduit is designed to be electrolytically corroded at one or more points so that while in contact with a body fluid, and the occlusive member may be released from the conduit. An inner electrode assembly can be positioned within the lumen of the conduit such that a distally positioned electrode is disposed adjacent to an electrolytic detachment point of the conduit.

The delivery conduit can be configured to pass one or more embolic elements therethrough for intrasaccular delivery. The embolic element may be passed through the conduit and delivered to the treatment site. Once the occlusive member and any embolic elements are deployed, current can be applied to the conduit to electrolytically corrode the conduit at the detachment zone. For example, the conduit can be electrically coupled to a positive terminal of a power supply, while the inner electrode assembly can be electrically coupled to a negative terminal of the power supply, such that in operation current passes from the conduit at the detachment zone to the inner electrode. After the conduit has been severed at the detachment zone, the conduit can be retracted, and the occlusive member may remain in position at the treatment site. In some embodiments, an inner liner and/or an outer sheath extend along at least a portion of the length of the conduit. The outer sheath can include a gap or opening that is aligned with the detachment zone such that the detachment zone of the conduit is exposed to bodily fluids while at the treatment site.

Specific details of systems, devices, and methods for treating intracranial aneurysms in accordance with embodiments of the present technology are described herein with reference to FIGS. 1A-13C. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. Overview of Systems of the Present Technology

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100*a* configured to be extracorporeally positioned during treatment and a distal portion 100*b* configured to be intravascularly positioned within a blood vessel (such as an intracranial blood vessel) at a treatment site at or proximate an aneurysm. The treatment system 100 may include a handle 103 at the proximal portion 100*a*, the occlusive member 102 at the distal portion 100*b*, and a plurality of elongated shafts or members extending between the proximal and distal portions 100*a* and 100*b*. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

Figure 1B:
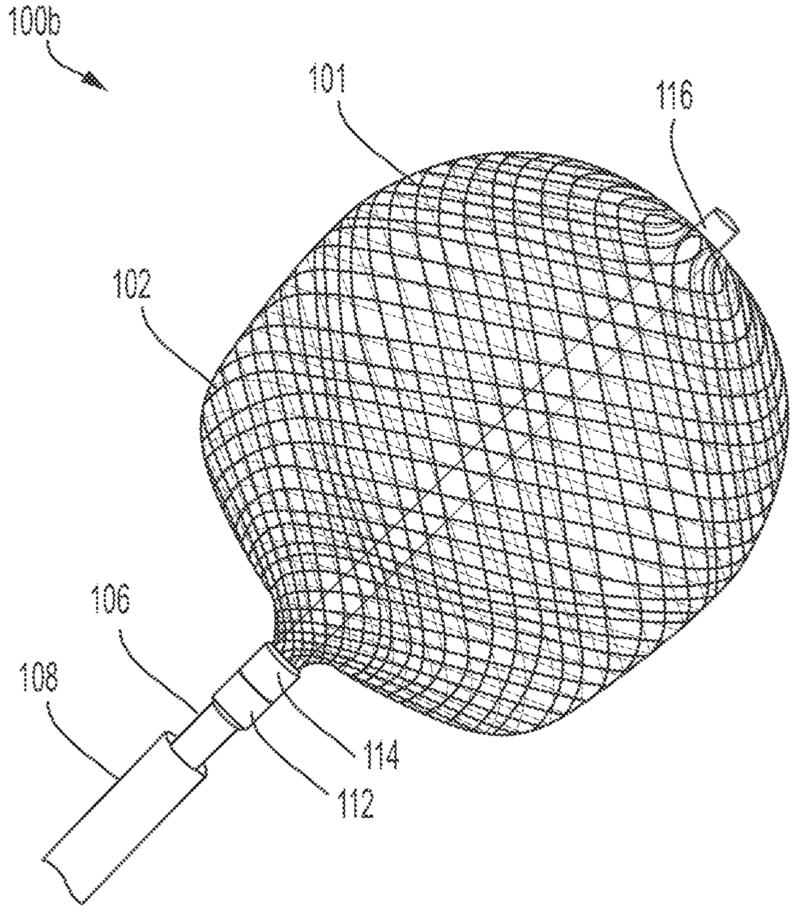
FIG. 1B shows an enlarged view of a distal portion of the treatment system of FIG. 1A in accordance with the present technology.

FIG. 1B is an enlarged view of the distal portion 100*b* of the treatment system 100. Referring to FIGS. 1A and 1B together, the occlusive member 102 may be detachably coupled to a distal portion of the elongated member 106. For example, the elongated member 106 may include a first coupler 112, and the occlusive member 102 may include a second coupler 114 configured to detachably couple with the first coupler 112. In some embodiments, the couplers 112, 114 can take the form of an electrolytic detachment mechanism, for example as described in more detail below with respect to FIGS. 4-8C. The treatment system 100 may further comprise a conduit 116 extending from the handle 103 (for example, via port 110) distally to the distal portion 100*b* of the treatment system 100. The conduit 116 is configured to deliver the embolic element (and/or one or more precursors thereof) through one or more components of the delivery system (e.g., the first or second elongated shafts 109, 108, the elongated member 106, etc.) to a position at the exterior of the occlusive member 102. As such, the embolic element may be positioned between the occlusive member 102 and an inner wall of the aneurysm cavity, as described in greater detail below. In some embodiments, the elongated member 106 serves as the conduit 116.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongated shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise an elongated tubular member having a lumen therein, for example a conduit. In some embodiments, the elongated member 106 may comprise any other suitable form such as a solid metal wire, an elongated tubular shaft, or any combination thereof.

In some embodiments, the elongated member 106 can comprise stainless steel, nitinol, or other metal or alloy. In some embodiments, the elongated member 106 can be surrounded over some or all of its length by a coating, such as, for example, polytetrafluoroethylene. In some examples, the elongated member 106 can be a hypotube or other conductive tubular member, and can include an outer insulative sheath and/or an inner insulative liner extending along a length of the elongated member 106. The elongated member 106 may have a diameter that is generally constant along its length, or the elongated member 106 may have a diameter that tapers radially inwardly, along at least a portion of its length, as it extends in a distal direction.

A power supply 113 may be coupled to a proximal portion of the elongated shaft 108, which can take the form of a conductive wire. The power supply 113 may also be coupled to a proximal portion of a handle or to the patient. A current can flow from the power supply 113, to a detachment zone at or near the occlusive member 102, and to a return path via an inner electrode assembly disposed within the conduit, as described in more detail below. Additionally or alternatively, the return electrode and associated return path can extend along the first elongated shaft 109, the second elongated shaft 108, and/or another structure extending near the detachment zone. Alternatively, the current from the detachment zone may flow to the patient, and subsequently to ground or to the power supply 113. For example, the return electrode can take the form of an external electrode (e.g., a needle, grounding pad, or other suitable structure) that can be coupled to the patient's body at a location outside the vasculature (e.g., the patient's skin).

Power supply 113, for example, may be a direct current power supply, an alternating current power supply, or a power supply switchable between a direct current and an alternating current. A positive terminal of a direct current power supply, as shown in FIG. 1, may be coupled to the proximal portion of the elongated shaft 108, 111 and a negative terminal of a direct current power supply may be coupled to the proximal portion of the handle. Power supply 113 may provide a current through the treatment system 100 to initiate an electrolytic process during use of the assembly in a fluid medium such as a bloodstream, which may be used as an electrolyte. A power supply, such as an alternating or direct current power supply, may additionally be used to initiate an electrothrombosis process.

A. Selected Examples of Occlusive Members

Figure 1C:
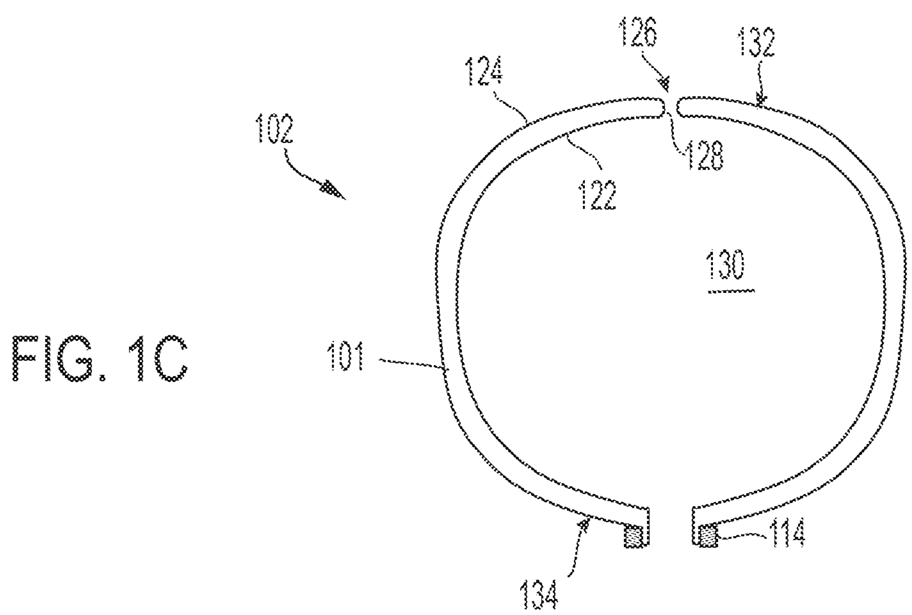
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
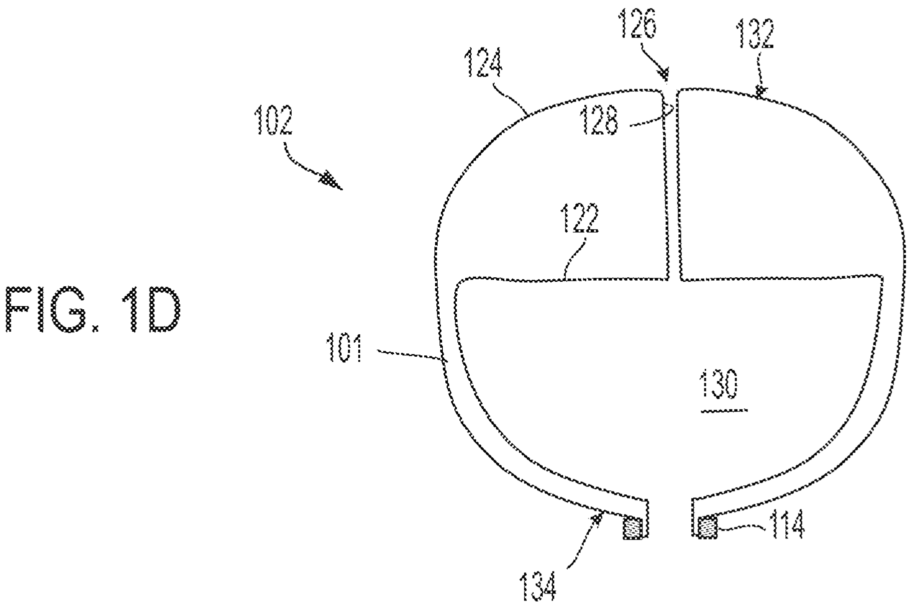
Figure 2:
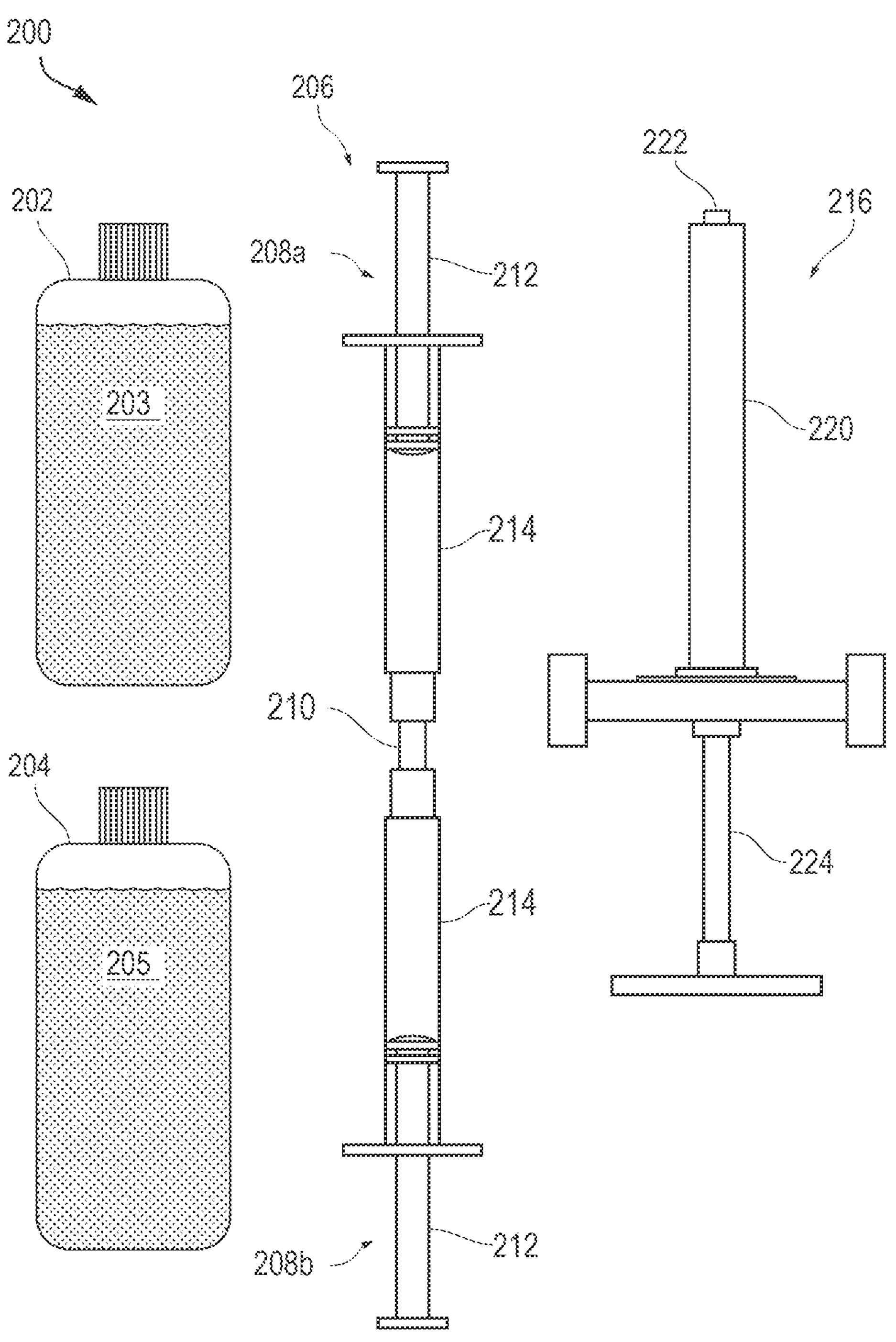
FIG. 2 shows an embolic kit according to the present technology.

The inner layer 124 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusion member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to the at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208*a*, 208*b*) and a coupler 210 extending between respective exit ports (not shown) of the mixing syringes 208. The mixing syringes 208*a*, 208*b* each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100*b* of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the kit 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MM imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

Additional details regarding suitable embolic element may be found in U.S. patent application Ser. No. 15/299,929, filed Oct. 21, 2016, the disclosure of which is incorporated herein by reference in its entirety.

II. Selected Methods for Treating Aneurysms

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state. Releasing the occlusive member 102 from the shaft 108 and allowing the occlusive member 102 to self-expand into a first expanded state may alternatively, or additionally, include withdrawing shaft 108 relative to the elongated member 106.

Figures 3A, 3B:
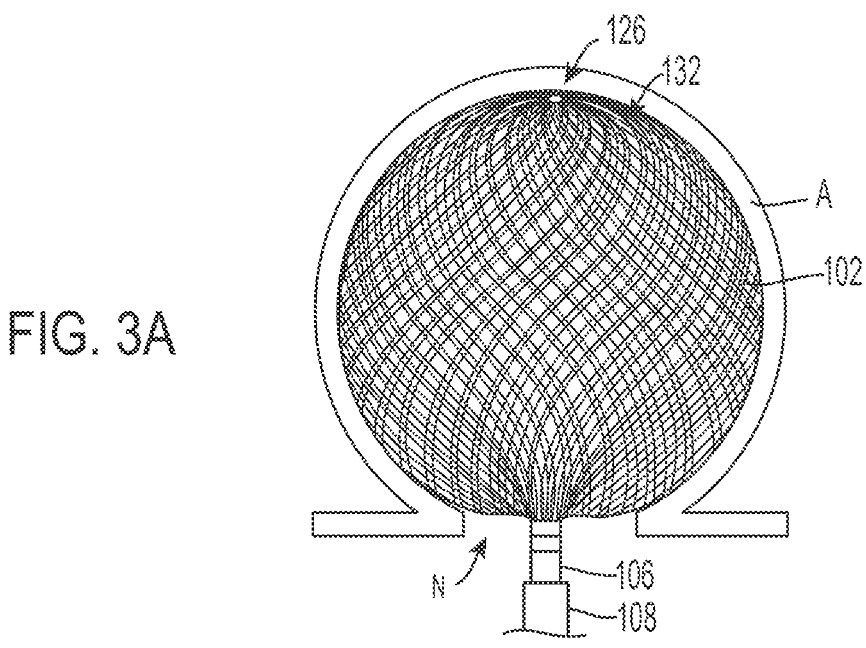
FIGS. 3A-3G depict an example method of treating an aneurysm with the treatment system of the present technology.

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W. Although the illustrated example shows a separate conduit 116 extending through a lumen of the elongated member 106, in other embodiments the elongated member 106 may itself form the conduit 116, e.g., by extending through a proximal hub of the occlusive member 102 and through the internal volume 130.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
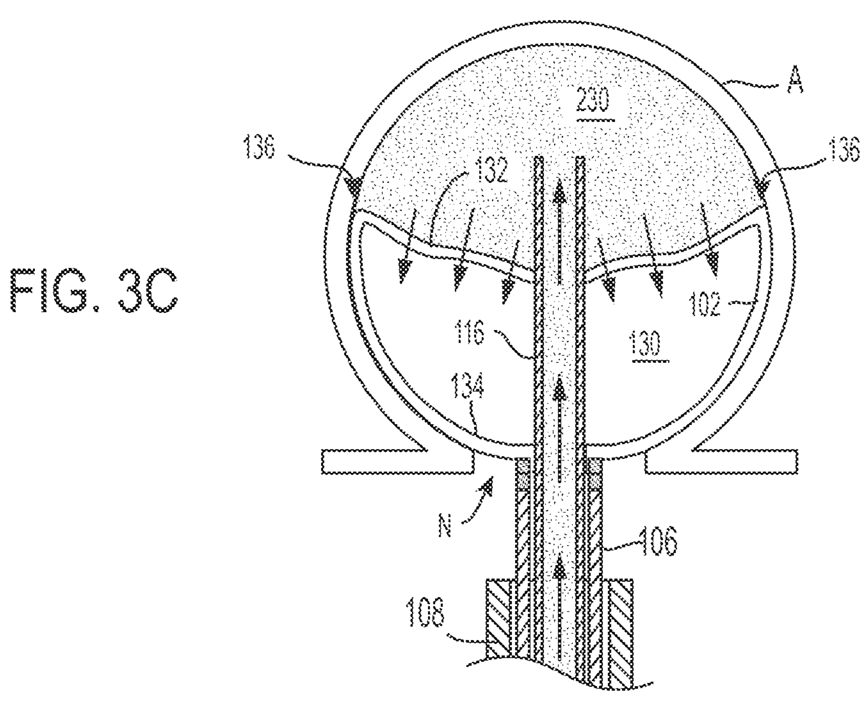
Figure 3D:
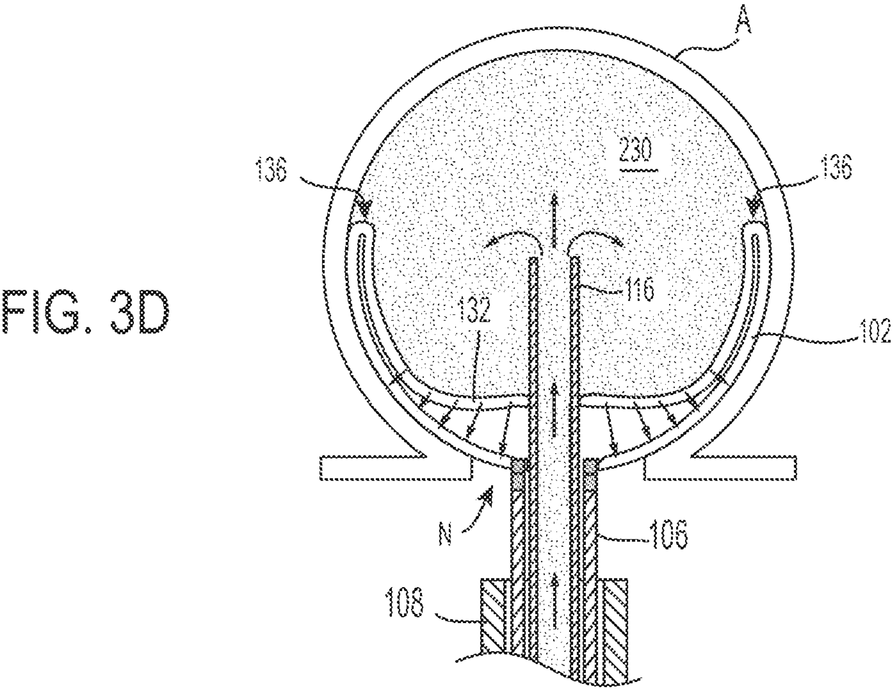

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figures 3E, 3F:
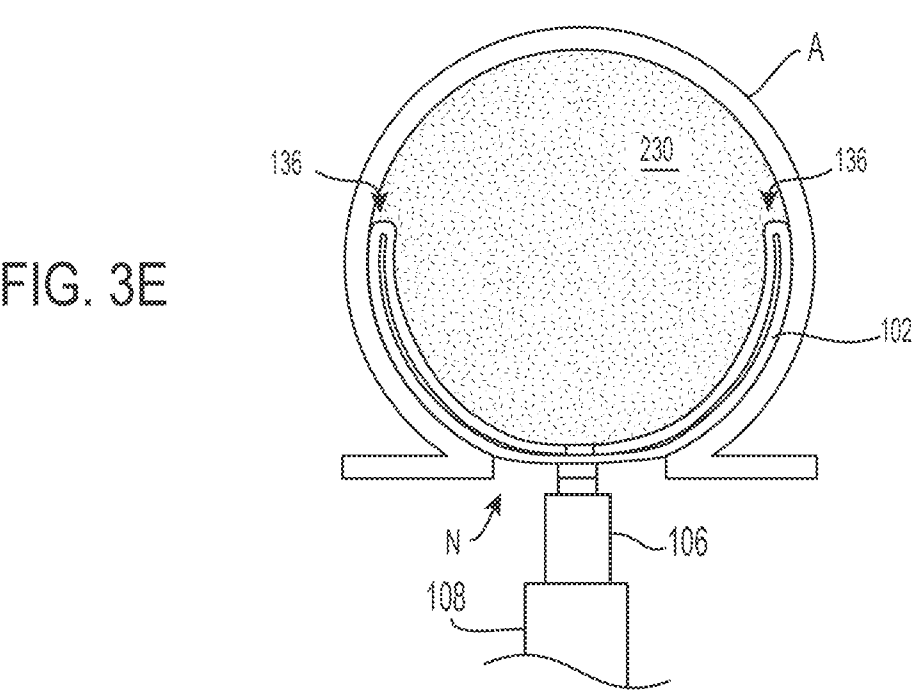

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusion member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
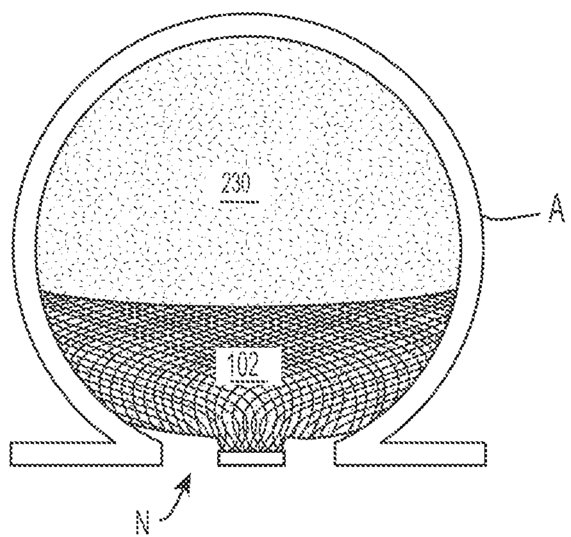

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A. For example, the occlusive member 102 may be detached from the elongated member 106 using any of the electrolytic detachment mechanisms described in more detail below. In some examples, at least a distal portion of the conduit 116 may remain in place following detachment (e.g., electrolytic severance) of the elongated member 106 and/or conduit 116.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive member 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. Example Systems with Electrolytic Detachment Mechanisms

Figures 4, 5:
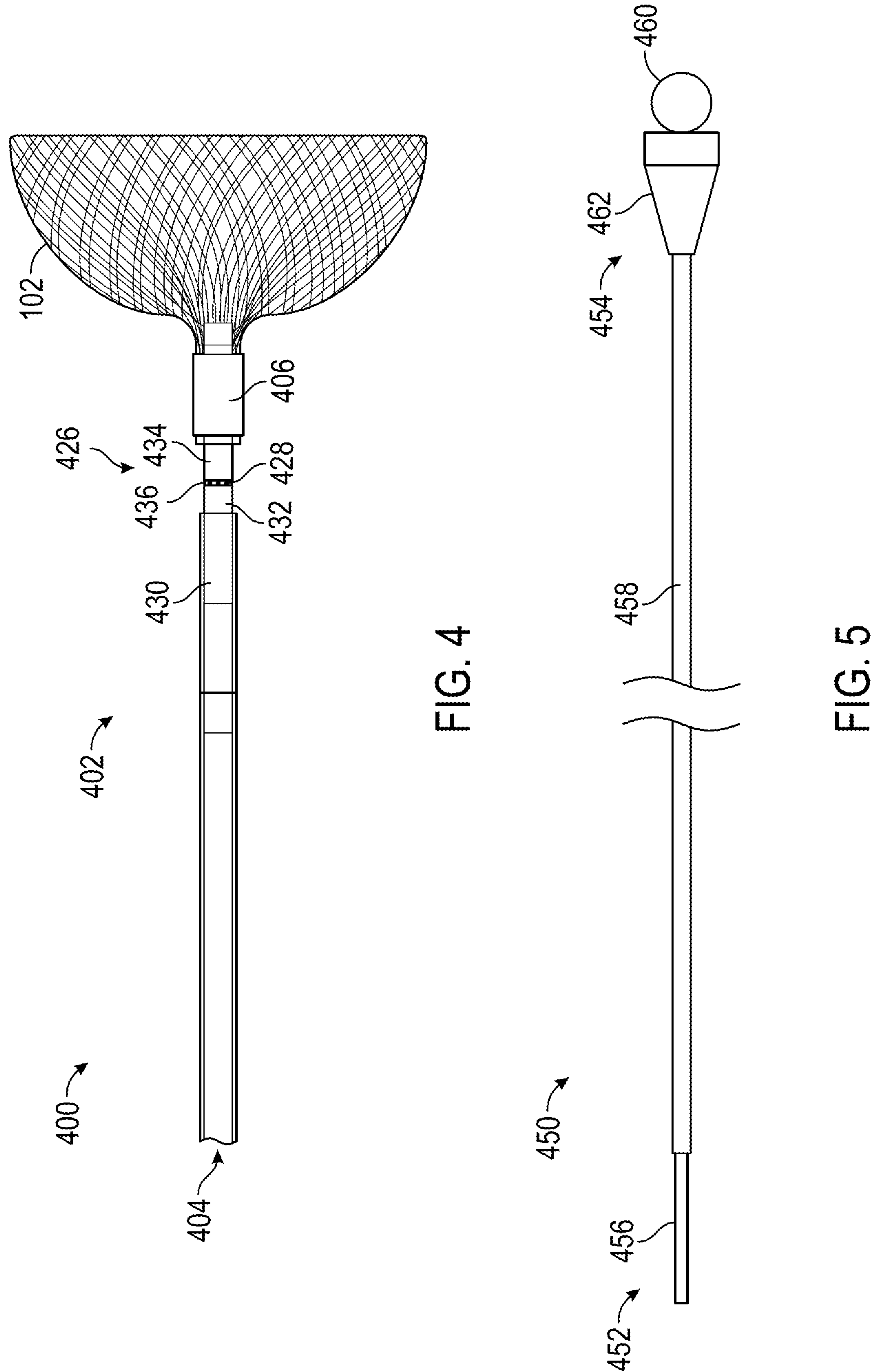
FIG. 4 shows a schematic side view of a treatment system including a conduit assembly in accordance with aspects of the present technology.
FIG. 5 shows a schematic side view of an inner electrode assembly in accordance with aspects of the present technology.

FIG. 4 shows a schematic side view of a treatment system 400, and FIG. 5 shows a side view an inner electrode assembly 450 of the treatment system 400 shown in FIG. 4. As described in more detail below, the treatment system 400 can include a conduit assembly 402 that is releasably coupled to the occlusive member 102. The inner electrode assembly 450 can be slidably disposed within the lumen of the conduit assembly 402. In operation, the treatment system 400 facilitates placement of the occlusive member 102 at the treatment site and utilizes electrolytic detachment to release the occlusive member 102 from the conduit assembly 402. As described in more detail below, a distal portion of the conduit assembly 402 may remain in place alongside the occlusive member 102 following electrolytic detachment. Furthermore, the conduit assembly 402 can facilitate introduction of an embolic element 230 (FIGS. 2-3G) therethrough for placement at the treatment site (e.g., within an aneurysm sac accompanying the occlusive member 102).

Although several examples refer to the use of electrolytic detachment, in various embodiments other techniques can be used to sever a conduit and release the occlusive member 102. For example, instead of or in addition to electrolytic detachment, embodiments of the present technology may utilize thermal detachment, mechanical detachment, chemical detachment, or any other suitable detachment techniques.

Figures 6A, 6B, 6C:
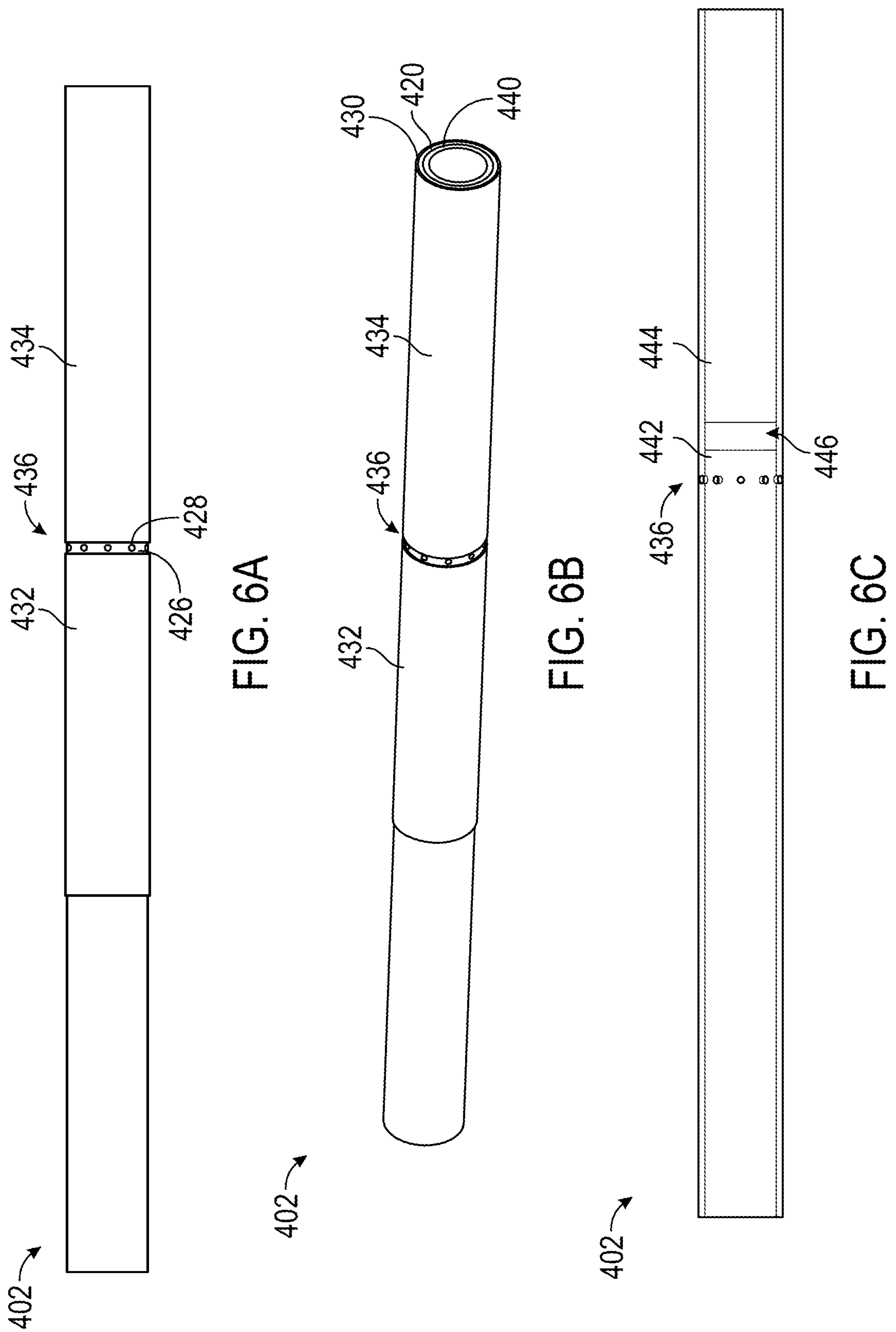
FIG. 6A shows a side view of a portion of the conduit assembly depicted in FIG. 4
FIG. 6B shows a side perspective view of the portion of the conduit assembly shown in FIG. 6A.
FIG. 6C shows a side view of the conduit assembly shown in FIGS. 6A and 6B, with an outer insulation portion omitted for clarity.

As noted above, FIG. 4 illustrates a side view of the treatment system 400, which includes a conduit assembly 402 and an inner electrode assembly 450. A side view of the inner electrode assembly 450 is shown in FIG. 5. FIG. 6A illustrates an enlarged side view of a portion of the conduit assembly 402. FIG. 6B illustrates an enlarged perspective view of the portion of the conduit assembly 402. FIG. 6C illustrates an enlarged view of a portion of the conduit assembly 402 with the outer sheath omitted, and the conduit shown in transparency to depict the inner liner therein.

Referring to FIGS. 4-6C together, the conduit assembly 402 can take the form of an elongated tubular member defining a lumen 404 therein. The inner electrode assembly 450 can be slidably received within the lumen 404 as described in more detail below. The conduit assembly 402 can be coupled to a proximal hub 406 of the occlusive member 102, such that the lumen 404 extends distally beyond the proximal hub 406. In some embodiments, the hub 406 can include an inner band that circumferentially surrounds a portion of the conduit assembly 402, and an outer band that surrounds the inner band, such that proximal portions of the layers of the occlusive member 102 are grasped between the inner and outer bands of the hub 406. Such bands can be made of any suitable material, for example being polymeric or metallic, and optionally may be radiopaque to facilitate visualization of the system 400 as it advanced through the vasculature. The bands can be crimped, with or without an adhesive or weld, to secure them in place. In operation, an embolic element can be introduced via the lumen 404 into the treatment site (e.g., within an aneurysm sac) and adjacent the occlusive member 102. In some examples, hub 406 can have an inner diameter of about 0.020 inches and an outer diameter of about 0.023 inches.

In various embodiments, the conduit assembly 402 can include a single tubular member or a plurality of tubular members arranged coaxially. Moreover, any one of the tubular members can be monolithic or can be formed of multiple separate components joined together. Additionally or alternatively, some or all of the tubular member(s) can include one or more coatings along some or all of their respective lengths. In some embodiments, one or more of the tubular members can be slidably moveable with respect to other tubular members. Alternatively or additionally, one or more of the tubular members can be fixed (e.g., non-slidably coupled) with respect to the other tubular members.

In the embodiment illustrated in FIG. 4, the conduit assembly 402 includes a conduit 420 which takes the form of an elongated tubular member such as a hypotube. An outer sheath 430 extends along a radially outer surface of the conduit 420 over at least a portion of its length, and an inner liner 440 (FIG. 6C) extends along a radially inner surface of the conduit 420. As described in more detail below, the conduit 420 can include a detachment zone 426 configured to be electrolytically corroded when current is supplied to the conduit 420. The outer sheath 430 and/or the inner liner 440 can be electrically insulative such that current carried by the conduit 420 is confined to the conduit 420 and focused at the detachment zone 426. When in the presence of an electrolytic medium, such as blood, current passes from the conduit 420 to the surrounding media through the detachment zone 426.

As seen in FIG. 5, the inner electrode assembly 450 extends from a proximal end portion 452 to a distal end portion 454, and is configured to be slidably inserted into the lumen 404 of the conduit assembly 402. The inner electrode assembly 450 includes an inner conductive wire 456 (e.g., a rod, shaft, or other elongate conductive member) having an exposed proximal portion that can be coupled to a power supply and an insulation material 458 that partially or completely surrounds the wire 456 along at least a portion of its length. The material 458 can be insulative (e.g., polyimide, PTFE, parylene) or any other suitable electrically non-conductive material. At the distal end portion 454, the inner electrode assembly 450 includes a distally located electrode 460 and a plug element 462 disposed proximal to the electrode 460. The electrode 460 can be made of any suitable conductive material (e.g., stainless steel, nitinol, etc.) and can be configured to serve as a return electrode when the conduit 420 is connected to a positive terminal of a power supply, the wire 456 is connected to a negative terminal of the power supply, and the electrode 460 is disposed adjacent the detachment zone 426 of the conduit 420.

In various embodiments, the inner electrode assembly 450, including the wire 456 and/or the electrode 460, can include one or more of the following electrically conductive materials: ceramic materials, plastics, base metals or alloys thereof, for example stainless steel or nitinol. The electrode 460 can comprise a portion of the inner electrode assembly 450 that is electrically uninsulated. In various embodiments, the electrode 460 has an outer cross-sectional dimension that is larger than an outer cross-sectional dimension of the wire 456 and/or the insulation 458. In one example, the wire 456 can have an outer diameter of approximately 0.003" and the electrode 460 can have an outer diameter of approximately 0.010". As such, the electrode 460 can have an outer diameter that is at least 2, 3, 4, 5, or more times larger than an outer diameter of the wire 456. In the illustrated example, the electrode 460 takes the form of a ball-shaped member and can be substantially spherical. In various embodiments, the electrode 460 can assume other forms, and may optionally include an atraumatic distal face and/or an outer dimension that tapers in the distal direction.

The plug element 462 can be made of and/or coated with an electrically insulative material. In the illustrated example, thee plug 462 has a maximum outer cross-sectional dimension that is slightly larger than the largest cross-sectional dimension of the electrode 460. In various embodiments, the plug element 462 can have a maximum cross-sectional dimension that is substantially equal to or smaller than the maximum outer cross-sectional dimension of the electrode 460. The plug element 462 can also taper in the proximal direction. A distal face of the plug element 462 can be configured to substantially occlude the lumen 404 of the conduit assembly 402 such that, when the plug element 462 is positioned within the lumen, an embolic element (e.g., a liquid embolic) is substantially prevented from passing through the lumen 404 beyond the plug element 462. This can advantageously reduce the risk of leaking an embolic element from the conduit assembly 402 following severance of the detachment zone 426.

In various embodiments, the conduit assembly 402 can have a length sufficient to permit the occlusive member 102 to be positioned at an intravascular treatment site (e.g., within an aneurysm sac) while a proximal end of the conduit assembly 402 extends outside the patient's body. For example, the conduit assembly 402 can have a length of greater than about 50 inches, 60 inches, 70 inches, or 80 inches. The conduit assembly 402 can have an outer diameter suitable to permit the assembly 402 to be slidably advanced through a delivery catheter. For example, the conduit assembly 402 can have an outer diameter of less than about 0.027 inches, less than about 0.021 inches, or less than about 0.017 inches.

In the example shown in FIG. 4, the conduit assembly 402 extends through the hub 406 of the occlusive member 102, with a stepped down diameter at the hub 406 resulting in a narrower lumen 404 in a distal portion of the conduit assembly 402 that extends through the hub 406 and distal to the hub 406. In some embodiments, this stepped-down diameter can result from crimping the hub 406 over the conduit assembly 402. In other embodiments, however, the conduit assembly 402 need not have such a stepped-down inner and/or outer diameter. For example, the conduit assembly 402 can have an outer diameter and/or an inner diameter that is substantially constant along its length, or that tapers gradually along some or all of its length.

As noted above, the conduit assembly 402 includes a conduit 420, which can be radially disposed between an outer sheath 430 and an inner liner 440. The conduit 420 includes a proximal portion 422, a distal portion 424, and a detachment zone 426 disposed axially between the proximal portion 422 and the distal portion 424. In some embodiments, the conduit 420 can be an electrically conductive tubular member, for example a hypotube, catheter, or other suitable tubular member. In some embodiments, a portion of the conduit 420, including the detachment zone 426, can be coated with a conductive material, such as carbon, gold, platinum, tantalum, combinations thereof, and the like. One or more metallic coatings can be applied using known plating techniques. In various embodiments, the conduit 420 can have cuts (e.g., a spiral cut, a groove, etc.) along at least a portion of its length to achieve the desired mechanical properties (e.g., column strength, flexibility, kink-resistance, etc.).

The conduit 420 can be dimensioned to facilitate intravascular advancement to the treatment site and to accommodate a lumen 404 sufficient to permit advancement of embolic element(s) therethrough. In some embodiments, the conduit 420 can have a wall thickness of between about 0.0005 inches and about 0.0015 inches, or about 0.001 inches in some examples. The conduit 420 can have an outer diameter in the proximal portion of less than about 0.027 inches, less than about 0.021 inches, or less than about 0.017 inches. Additionally or alternatively, the conduit 420 can have an inner diameter of less than about 0.015 inches, less than about 0.012 inches, less than about 0.010 inches, or less than about 0.008 inches. In some embodiments, the conduit 420 can have a stepped-down diameter where the conduit 420 passes through the hub 406. For example, the conduit 420 can have an outer diameter of about 0.016 inches proximal to the hub 406, and an outer diameter of about 0.014 inches within the hub 406. This reduced diameter can be achieved by crimping the bands of the hub 406 over the conduit 420, or by forming the conduit 420 with a stepped-down profile prior to coupling the conduit 420 to the hub 406.

The conduit 420, including the detachment zone 426, can include one or more of the following materials: ceramic materials, plastics, base metals or alloys thereof, for example stainless steel or nitinol. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the treatment system can be electrically conductive.

In some embodiments, the detachment zone 426 can include features to facilitate electrolytic severability, such as features configured to reduce a time that current must be supplied to the conduit 420 before the conduit is severed at the detachment zone 426. In some embodiments, the detachment zone 426 can include a sidewall having one or more openings 428 formed therein, which can take the form of one or more windows, slits, apertures, holes, or other such features. The openings 428 can both increase the surface-area-to-volume ratio at the detachment zone 426, and can also reduce the overall amount of material forming the sidewall of the conduit 420 at the detachment zone 426. As a result, the sidewall material of the conduit 420 at the detachment zone 426 may be more readily electrolytically corroded when current is supplied to the conduit 420 and the detachment zone 426 is exposed to an electrolytic medium such as blood. Additionally or alternatively to the openings 428, the detachment zone 426 can include a reduced sidewall thickness of the conduit 420, such as by forming a groove or other recess around some or all of a circumference of the conduit 420, and/or otherwise provide a lower material density than the proximal and distal portions 422, 424 of the conduit 420. In some embodiments, the detachment zone 426 can be surface treated (e.g., using laser or chemical treatment) to create a microstructure at the detachment zone 426 that differs from that of the proximal and distal portions 422, 424 of the conduit 420 to facilitate electrolytic detachment. For example, the detachment zone 426 can have a microstructure having a lower crystallinity than each of the conduit proximal portion 422 and conduit distal portion 424. As another example, the detachment zone 426 can have a microstructure that is more amorphous than each of the conduit proximal portion 422 and conduit distal portion 424.

According to some embodiments, portions of the conduit 420 can be covered with an electrically insulative material. For example, a sheath 430 that is made of or includes an electrically insulative material can extend over a radially outer surface of the conduit 420 along at least a portion of the length of the conduit 420. For example, the sheath 430 can include a proximal portion 432 that circumferentially surrounds an outer surface of the conduit proximal portion 422. The sheath 430 can also include a distal portion 434 that circumferentially surrounds an outer surface of the conduit distal portion 424. A void or gap 436 can separate the sheath proximal and distal portions 432, 434. In some embodiments, the sheath proximal and distal portions 432, 434 can be discrete members that are not connected to one another, while in other embodiments the proximal and distal portions 432, 434 may be connected across the gap 436, for example via connecting strands of material.

The sheath 430 can be fully or partially made of an electrically nonconductive or insulative polymer, such as polyimide, polypropylene, polyolefins, combinations thereof, and the like. In some embodiments, the sheath 430 takes the form of an extruded polymeric tube (e.g., PTFE), and the sheath 430 extends distally beyond the hub 406 and distally beyond a distal end of the conduit 420. Accordingly, in some embodiments, the sheath 430 can define the distal opening of the conduit assembly 402. In some embodiments, the distal end of the sheath 430 is disposed adjacent or distal to a distal end of the occlusive member 102 when the occlusive member 102 is in its expanded state. According to some embodiments, the distal end of the sheath 430 is disposed adjacent or distal to a distal end of the occlusive member 102 when the occlusive member 102 is in its low-profile state.

The sheath 430 can be dimensioned to facilitate intravascular advancement to the treatment site and to accommodate a lumen 404 sufficient to permit advancement of embolic element(s) therethrough. In some embodiments, the sheath 430 can have a wall thickness of between about 0.0005 inches and about 0.002 inches, or about 0.0015 inches in some examples. The sheath 430 can have an outer diameter in the proximal portion of less than about 0.027 inches, less than about 0.021 inches, less than about 0.017 inches, or less than about 0.015 inches. Additionally or alternatively, the sheath 430 can have an inner diameter of less than about 0.015 inches, less than about 0.012 inches, less than about 0.010 inches, or less than about 0.008 inches. As shown in FIG. 4B, the sheath 430 can have a stepped-down diameter, similar to that described above with respect to the conduit 420.

According to some embodiments, a gap 436 between the sheath proximal and distal portions 432, 434 leaves exposed the detachment zone 426 of the underlying conduit 420. When in contact with a body fluid, such as blood, the fluid serves as an electrolyte allowing current to be focused on the non-covered detachment zone 426. The sheath proximal and distal portions 422, 424 prevent exposure of the conduit proximal portion 422 and the conduit distal portion 424 to the fluid. Accordingly, electrical energy conducted along the conduit 420 is concentrated at the detachment zone 426, thereby reducing the time required to erode away the detachment zone 426. The sheath proximal and distal portions 432, 434 can be slidably disposed over, over-molded, co-extruded, sprayed on, or dip-coated with respect to the conduit 420.

The gap 436 between the sheath proximal portion 432 and the sheath distal portion 434 can be dimensioned so as to achieve the desired exposure of the underlying detachment zone 426. According to some embodiments, the gap 436 can be as small as 0.0005 inches and as large as 0.1 inches or longer. According to some embodiments, lengths of detachment zone 426 can be greater than 0.005 inches and/or less than 0.010 inches to provide sufficient exposure to achieve detachment times of less than 30 seconds.

According to some embodiments, the sheath distal portion 434 is disposed radially between the distal portion 424 of the conduit 420 and the hub 406 of the occlusive member 102.

As noted above, an inner liner 440 can be disposed radially inwardly of the conduit 420. The liner 440 can be an elongate tubular member and can be made of an electrically insulative material such as polyimide or other suitable polymer. In some embodiments, the liner 440 can have an inner surface defining the lumen 404 along at least a portion of the length of the conduit assembly 402. Accordingly, the inner surface of the liner 440 can be continuous and uninterrupted along its length, such that liquid embolic material passing therethrough is contained within the lumen 404 until it reaches a distal end of the liner 440. In particular, the liner 440 can provide a continuous and uninterrupted surface along the detachment zone 426 of the conduit 420, such that any embolic element(s) cannot pass from within the lumen 404 through the openings 428 in the conduit 420 at the detachment zone 426.

As best seen in FIG. 6C, in which the sheath 430 is omitted for clarity. The liner 440 can include a proximal portion 442 that circumferentially surrounds an outer surface of the conduit proximal portion 422. The liner 440 can also include a distal portion 444 that circumferentially surrounds an outer surface of the conduit distal portion 424. A void or gap 446 can separate the liner proximal and distal portions 442, 444. In some embodiments, the sheath proximal and distal portions 442, 444 can be discrete members that are not connected to one another, while in other embodiments the proximal and distal portions 442, 444 may be connected across the gap 446, for example via connecting strands of material. As shown in FIG. 6C, the liner gap 446 can be axially offset from the detachment zone 426 which includes the apertures 428, and may also be axially offset from the sheath gap 436. In various embodiments, the liner gap 446 can be axially aligned with the detachment zone 426 and/or with the sheath gap 436. In some implementations, providing an axial offset for the liner gap 446 can improve the distribution of current through the detachment zone and reduce the risk of a short occurring at a point where the electrode 460 directly contacts the conduit 420 at the detachment zone 426.

In various embodiments, the liner 440 can extend distally to be coterminous with the conduit 420 (e.g., at or adjacent a distal end of the hub 406), or alternatively the liner 440 can extend distally beyond the hub 406 and/or distally beyond a distal end of the conduit 420. The liner 440 can be made of or coated with a lubricious material to facilitate advancement of embolic element(s) therethrough. In some embodiments, the liner 440 takes the form of an extruded polymeric tube (e.g., PTFE) or other suitable electrically insulative material. Additionally or alternatively, the inner liner 440 can be co-extruded, sprayed on, or dip-coated with respect to the conduit 420.

The liner 440 can be dimensioned to facilitate intravascular advancement to the treatment site and to accommodate a lumen 404 sufficient to permit advancement of embolic element(s) therethrough. In some embodiments, the liner 440 can have a wall thickness of between about 0.0005 inches and about 0.0015 inches, or about 0.001 inches in some examples. The liner 440 can have an outer diameter in the proximal portion of less than about 0.027 inches, less than about 0.021 inches, or less than about 0.017 inches. Additionally or alternatively, the liner 440 can have an inner diameter of less than about 0.015 inches, less than about 0.012 inches, less than about 0.010 inches, or less than about 0.008 inches. As shown in FIG. 4B, the liner 440 can have a stepped-down diameter where the liner 440 passes through the hub 406, similar to that of the conduit 420 and sheath 430 described above.

In some embodiments, an embolic element can be delivered through the lumen 404 of the conduit assembly 402. The lumen 404 can terminate in a distal opening (not shown). As noted above, in some embodiments, the conduit assembly 402 can include an elongate flexible tubular member, for example a catheter, hypotube, polymer tube, etc. The lumen 404 can be coated with a lubricious material or lining to facilitate advancement of embolic element(s) therethrough. In some embodiments, the conduit assembly 402 is dimensioned such that the distal opening is disposed adjacent to, completely distal of, or at least partially distal of the occlusive member 102 while the occlusive member 102 is in the unexpanded state. The conduit assembly 402 can be dimensioned and configured such that the distal opening is disposed at distal to the hub 406 of the occlusive member 102, such that embolic element(s) delivered therethrough can be delivered to a region adjacent or distal of the occlusive member 102.

Figure 7A:
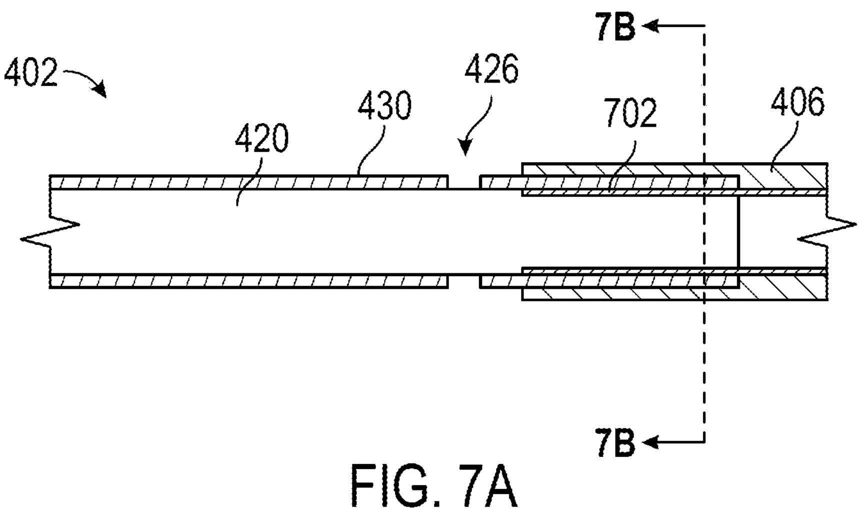
FIG. 7A shows a schematic side view of a distal portion of a conduit assembly in accordance with aspects of the present technology.
Figure 7B:
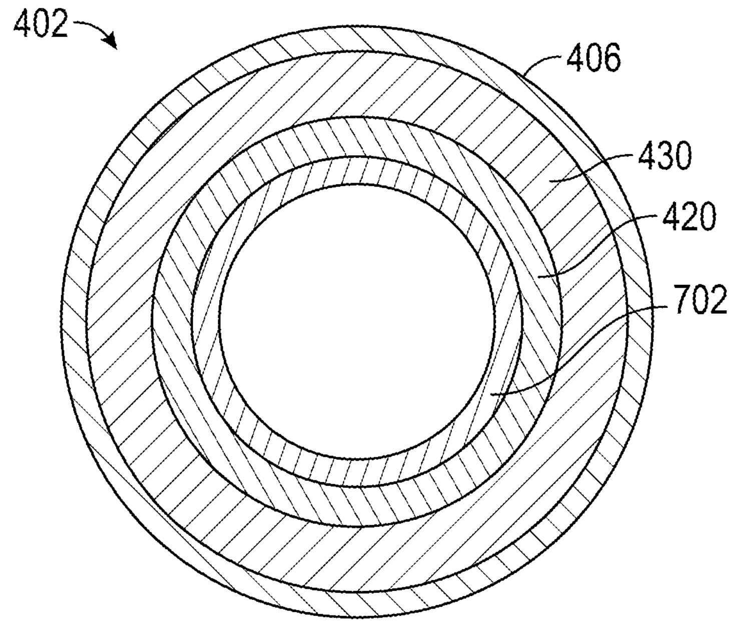
FIG. 7B shows a cross-sectional view taken along line 7B-7B shown in FIG. 7A.

FIG. 7A shows a schematic side view of a distal portion of the conduit assembly 402, and FIG. 7B shows a cross-sectional view taken along line 7B-7B shown in FIG. 7A. FIGS. 7A and 7B illustrate an arrangement of the conduit assembly 402 at its distal end where the conduit 420 mates with the hub 406 of the occlusive member. Because current is delivered to the conduit 420 and it may be desirable to focus current at the detachment zone, it can be beneficial to provide a distal cap that prevents current from leaking out of a distal end of the conduit 420. As noted previously, the conduit 420 can be covered along at least a portion of its length by an insulative sheath 430, with a gap in the sheath at the detachment zone 426 of the conduit 420. Distal to the detachment zone 426, the conduit assembly 402 can include an inner insulation material 702 that extends circumferentially around the lumen of the conduit 420 and extends distal to a distal end of the conduit 420. Distal to the distal end of the conduit 420, the insulation material 702 can be bonded with an overlying insulation material (not shown) disposed beneath the hub 406. A heat treatment can be used to cause the overlying insulation material (and/or optionally the inner insulation material 702) to reflow to adhere to the inner insulation material 702. In some embodiments, the inner insulation material 702 can have a higher melting point than the outer insulation material coupled to the hub 406, such that it is possible to reflow the outer insulation material without reflowing the inner insulation material 702. After reflowing, the hub 406 is coated on its inner surface with the outer insulation material, which is in direct contact with the inner insulation material 702 in a manner that ensures that the distal end of the conduit 420 is electrically insulated.

Figure 8A:
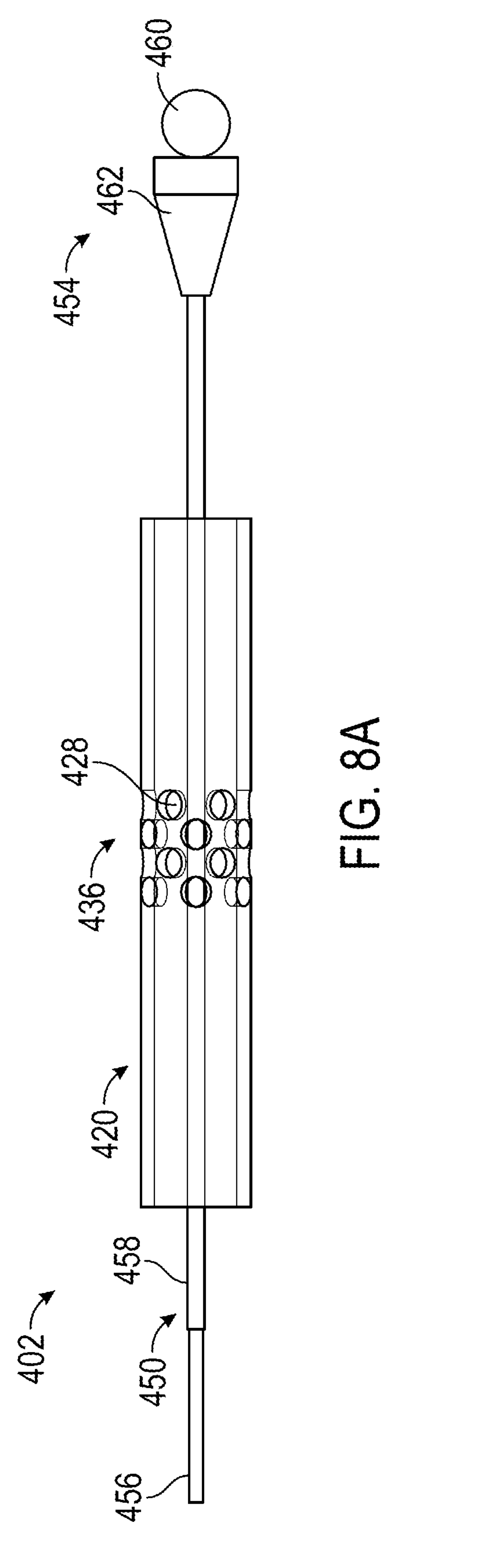
FIGS. 8A and 8B show side views of an inner electrode assembly extending through a conduit in accordance with aspects of the present technology.
Figure 8B:
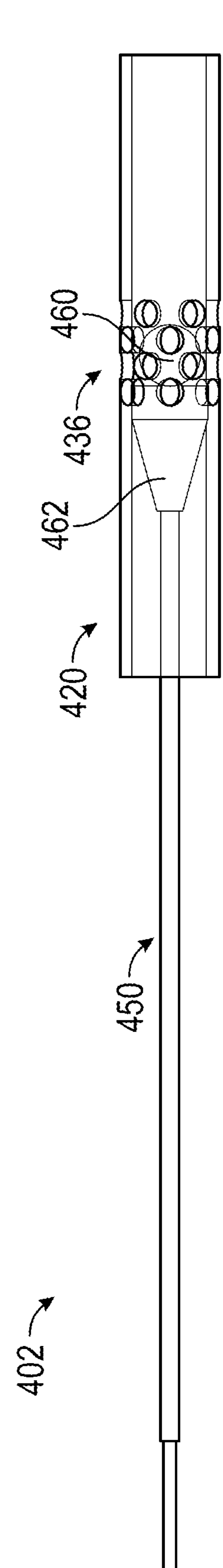

FIGS. 8A and 8B show side views of the inner electrode assembly 450 extending through the conduit 420. In each of these figures, only a portion of the conduit 420 is shown for clarity. In FIG. 8A, the electrode 460 and the plug element 462 of the inner electrode assembly 450 are disposed distal to the detachment zone 436, while in FIG. 8B the inner electrode assembly 450 has been proximally retracted with respect to the conduit 420 such that the electrode 460 is disposed adjacent to (e.g., substantially axially aligned with) the detachment zone 436. In some embodiments, the inner electrode assembly 450 can be arranged in the first configuration shown in FIG. 8A while the embolic element (e.g., a liquid embolic) is advanced through the conduit 420 and to the treatment site (e.g., an aneurysm sac). Because the electrode 460 and plug element 462 can be positioned distal to a distal end of the conduit 420, the electrode 460 and plug element 462 do not block delivery of the embolic element through the conduit 420. Once the embolic element delivery is complete, the inner electrode assembly 450 can be moved into the second configuration shown in FIG. 8B, at which point current can be supplied for electrolytically severing the conduit 420 at the detachment zone. Following detachment, the plug element 462 can advantageously prevent any remaining embolic element (e.g., a liquid embolic) within the conduit 420 from escaping at the opening created by the detachment process. In some embodiments, the plug element 462 can be positioned at or near a distal end of the remaining portion of the conduit 420 following detachment, and the conduit assembly 420 and the inner electrode assembly 460 can be proximally retracted from the treatment site in conjunction.

Figure 9A:
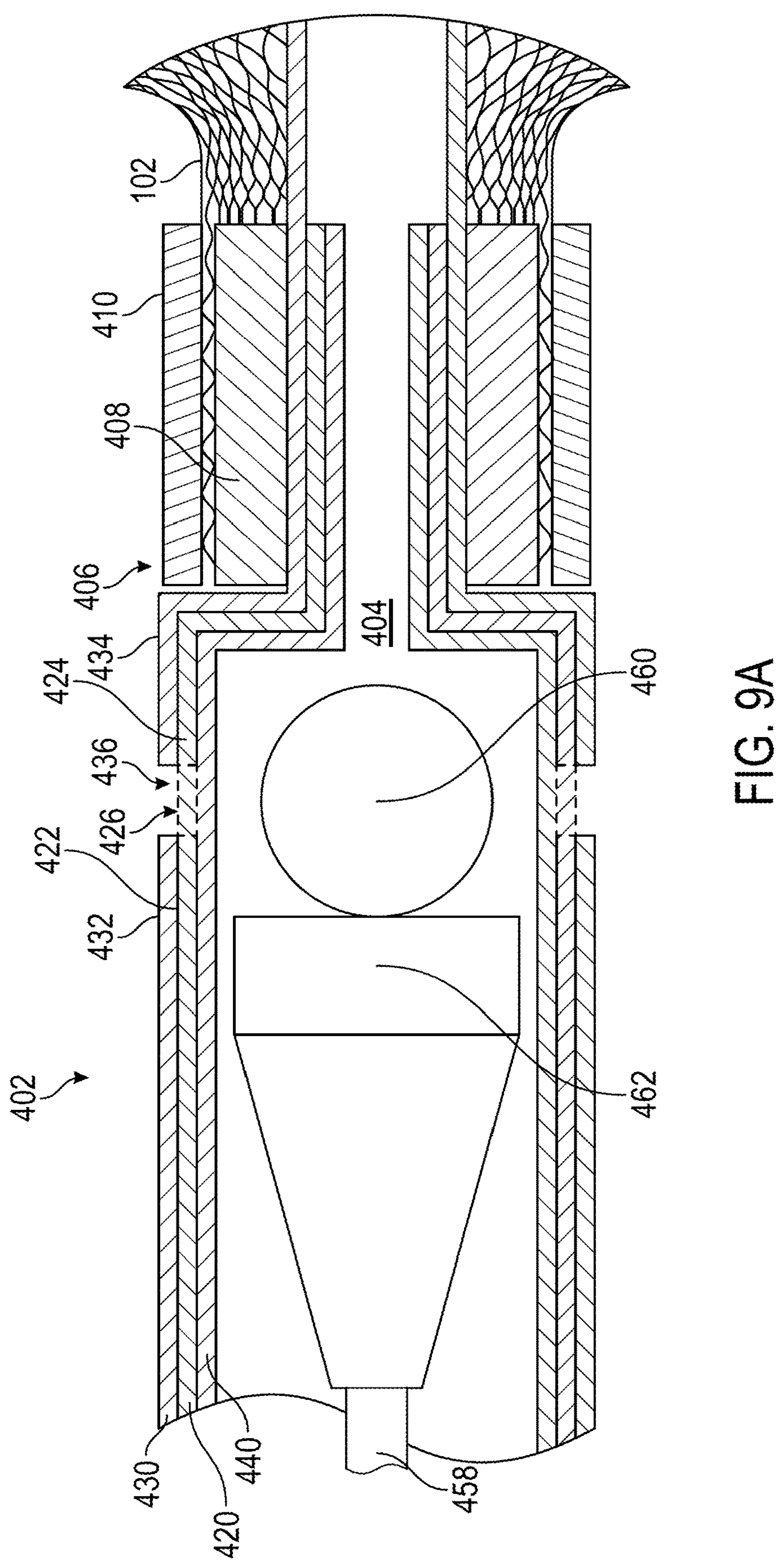
FIG. 9A shows a schematic side cross-sectional view of a treatment system in accordance with aspects of the present technology.

FIG. 9A is a cross-sectional illustration of a portion of the treatment system 400 with the inner electrode assembly 450 positioned such that the electrode 460 is disposed within the lumen 404 of the conduit 420 at an axial position that is substantially aligned with the detachment zone 426. In operation, the conduit 420 and the inner electrode assembly 450 can be coupled to a power source such that a voltage is applied across the conduit 420 and the electrode 460, which causes electrical current to flow between the detachment zone 426 and the electrode 460. This current facilitates electrolytic corrosion at the detachment zone 426, aided by the lower material density of the detachment zone 426 by virtue of the apertures 428 formed in a sidewall of the conduit 420.

In the example shown in FIG. 9A, the conduit assembly 402 extends through the hub 406 of the occlusive member 102, with a stepped down diameter at the hub 406 resulting in a narrower lumen 404 in a distal portion of the conduit assembly 402 that extends through the hub 406 and distal to the hub 406. In some embodiments, this stepped-down diameter can result from crimping the hub 406 over the conduit assembly 402. In other embodiments, however, the conduit assembly 402 need not have such a stepped-down inner and/or outer diameter. For example, the conduit assembly 402 can have an outer diameter and/or an inner diameter that is substantially constant along its length, or that tapers gradually along some or all of its length.

As shown in FIG. 9A, the inner band 408 of the hub 406 circumferentially surrounds and contacts the distal portion 434 of the sheath 430. The insulative sheath distal portion 434 can electrically isolate the occlusive member 102 from an electrical charge conducted along a length of the conduit 420. A proximal end of the sheath distal portion 434 may be positioned proximal to the hub 406, and a distal end of the sheath distal portion 434 may be positioned distal to the hub 406. Alternatively, the proximal end of the sheath distal portion 434 may be coterminous with a proximal end of the hub 406, and/or a distal end of the sheath distal portion 434 may be coterminous with a distal end of the hub 406.

In the example shown in FIG. 9A, the conduit assembly 402 extends through the hub 406 of the occlusive member 102, with a stepped down diameter at the hub 406 resulting in a narrower lumen 404 in a distal portion of the conduit assembly 402 that extends through the hub 406 and distal to the hub 406. In some embodiments, this stepped-down diameter can result from crimping the hub 406 over the conduit assembly 402. In other embodiments, however, the conduit assembly 402 need not have such a stepped-down inner and/or outer diameter. For example, the conduit assembly 402 can have an outer diameter and/or an inner diameter that is substantially constant along its length, or that tapers gradually along some or all of its length.

Figure 9B:
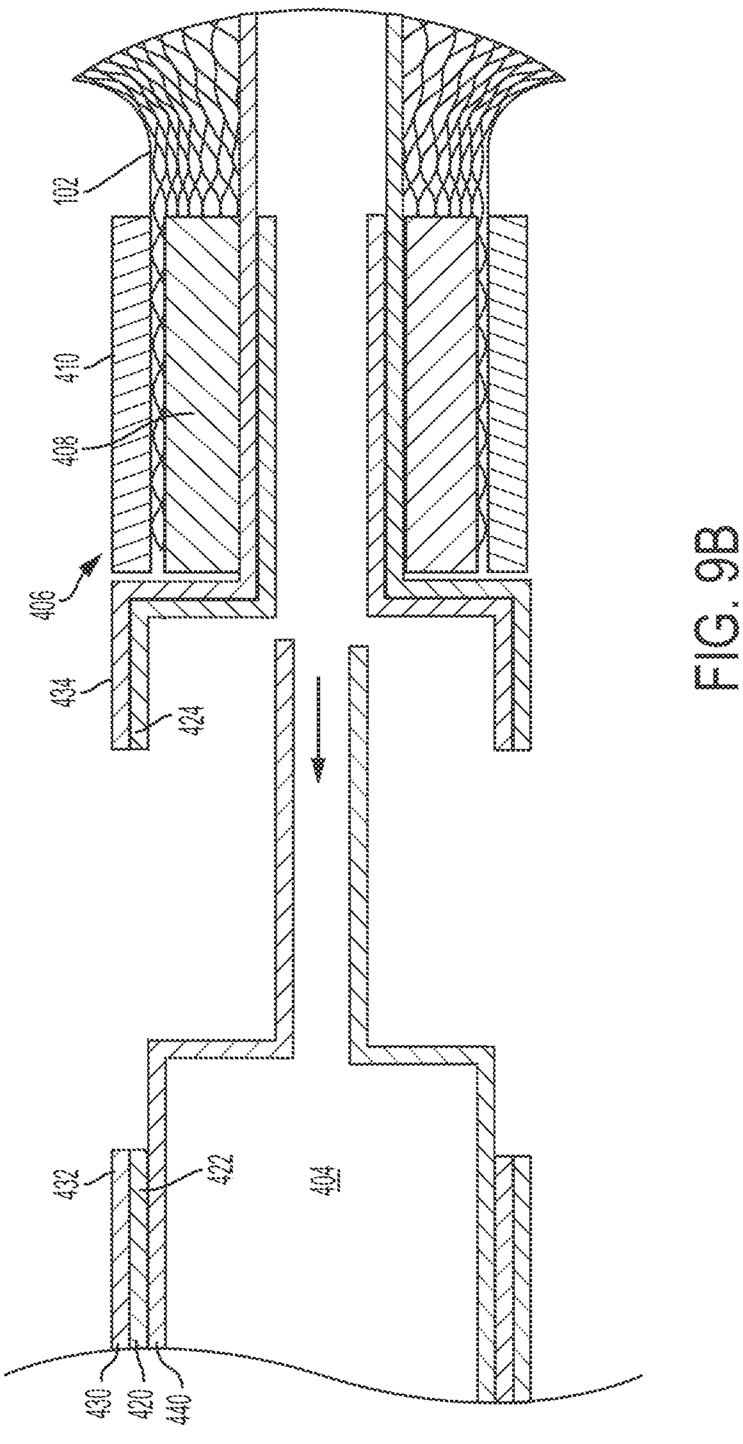
FIG. 9B shows a schematic side cross-sectional view of the treatment system of FIG. 9A after electrolytic detachment.

FIG. 9B illustrates the treatment system 400 with the conduit assembly 402 partially retracted following electrolytic severance of the conduit 420 at the detachment zone 426. As illustrated, the sheath proximal portion 422 and the conduit distal portion 424 can remain coupled to the hub 406 of the occlusive member 102, while the sheath proximal portion 422, conduit distal portion 424, and the liner 440 are retracted proximally. According to some embodiments, the conduit assembly 420 can be retracted through a surrounding catheter and removed from the body completely.

Figure 10:
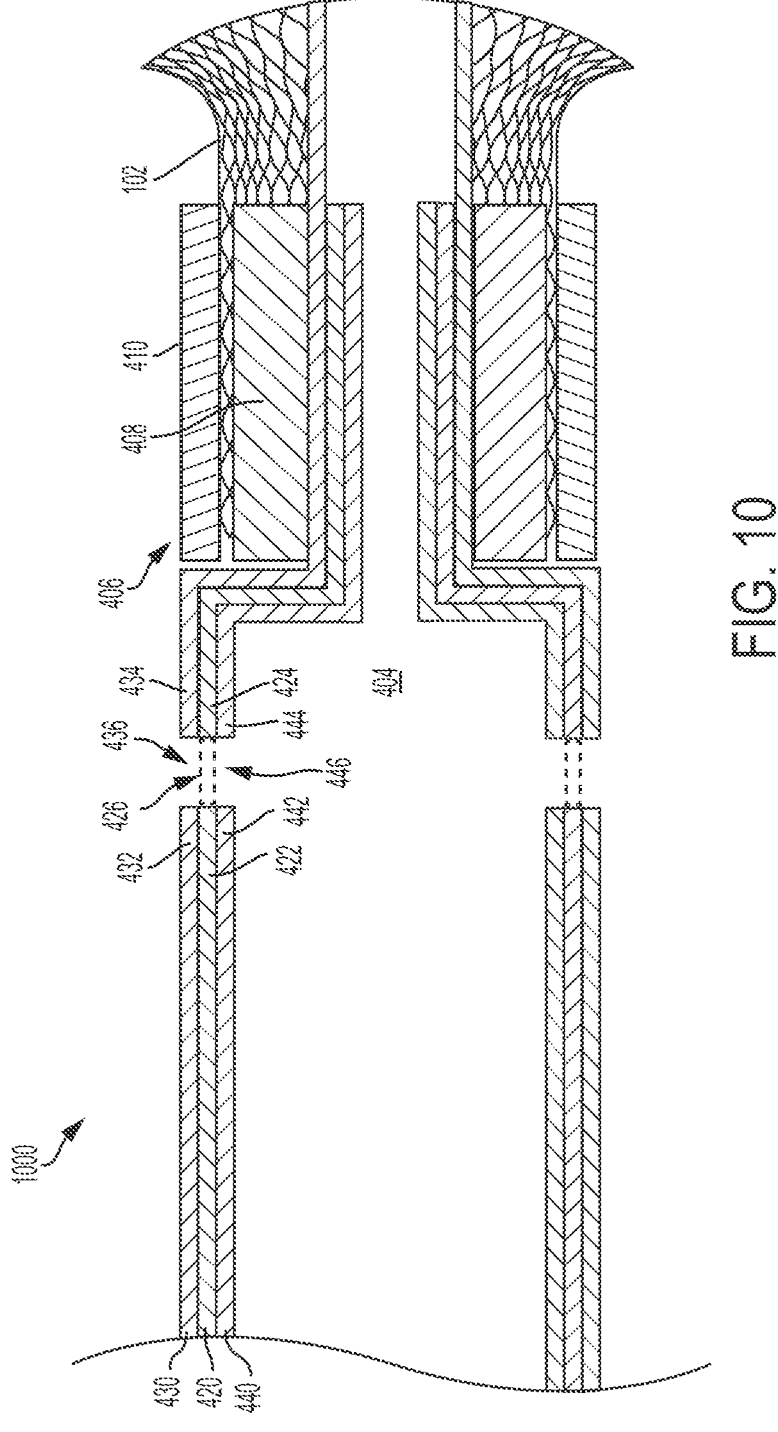
FIG. 10 shows a schematic side cross-sectional view of a portion of another embodiment of a conduit assembly.

FIG. 10 shows a schematic side view of another embodiment of a treatment system 1000 in accordance with aspects of the present technology. The treatment system 1000 can include several features that are generally similar to those of FIGS. 4-9B described above. However, in the treatment system 1000 shown in FIG. 10, the liner 440 includes a proximal portion 442 and a distal portion 424 that are spaced apart from one another by a gap 446 that is axially aligned with the detachment zone 426. In this configuration, following electrolytic severance of the conduit 420 at the detachment zone 426, the liner distal portion 444 may remain in place along with the occlusive member 102, the conduit distal portion 424, and the sheath distal portion 434. As such, the liner proximal portion 442 can be retracted along with the conduit proximal portion 422 and sheath proximal portion 432.

Figure 11:
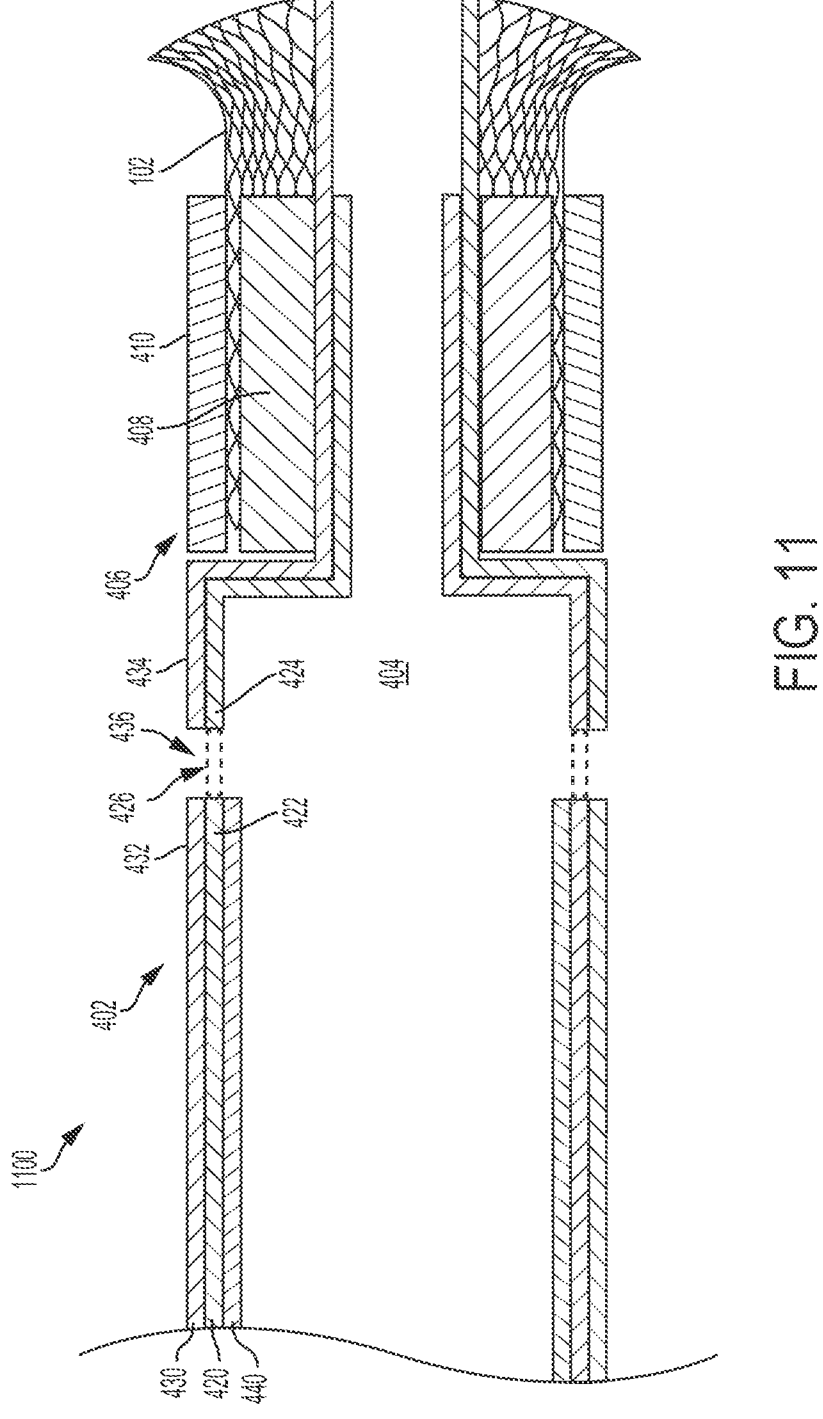
FIG. 11 shows a schematic side cross-sectional view of a portion of another embodiment of a conduit assembly.

FIG. 11 shows a schematic side view of another embodiment of a treatment system 1100 in accordance with aspects of the present technology. The treatment system 1100 can include several features that are generally similar to those of FIGS. 4-10 described above. However, in the treatment system 1100 shown in FIG. 11, the liner 440 terminates at or proximal to the detachment zone 426. In this configuration, the lumen 404 is defined by the liner 440 along a portion of the length of the treatment system 1100, and is defined by the inner surface of the conduit 420 along a distal portion of the conduit assembly 402.

Figure 12:
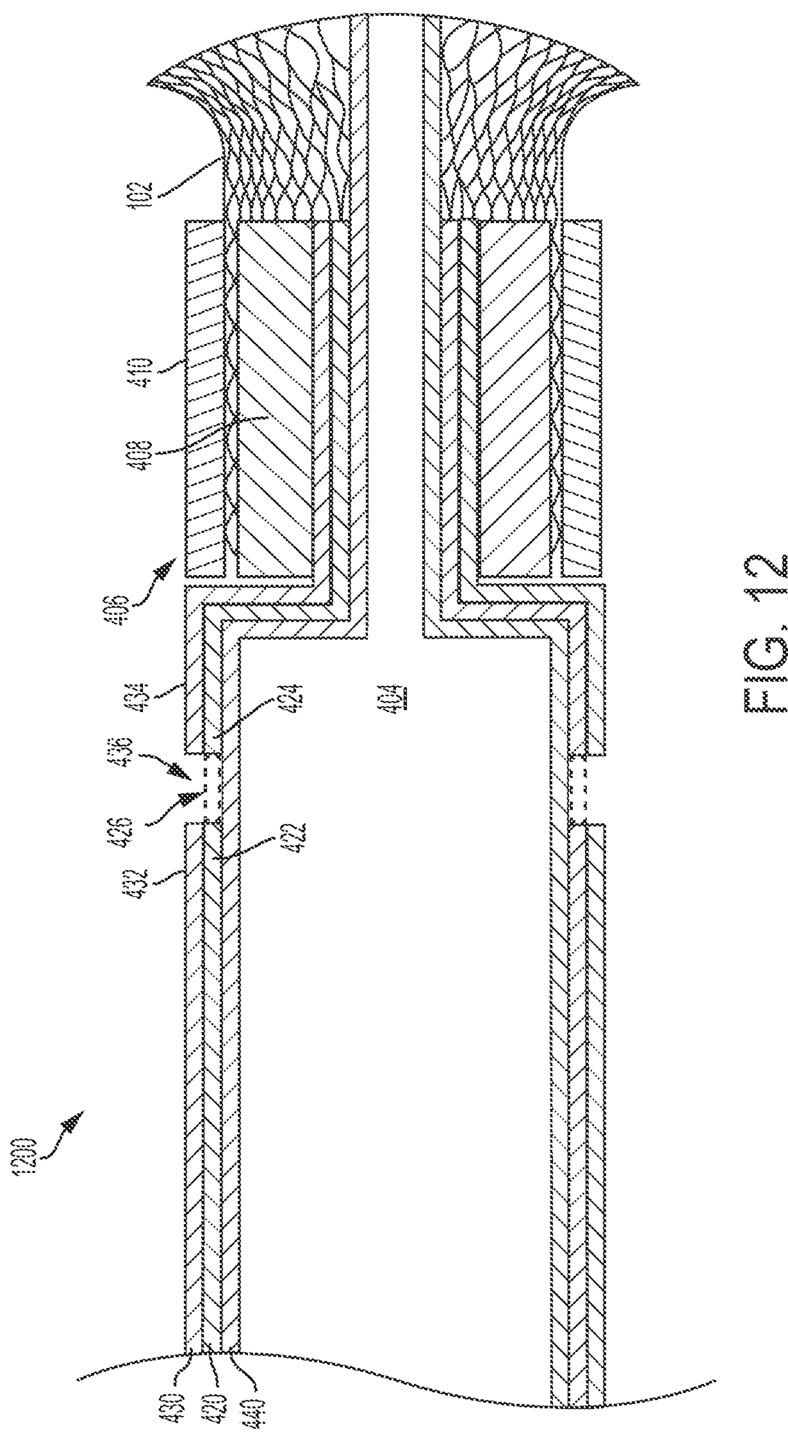
FIG. 12 shows a schematic side cross-sectional view of a portion of another embodiment of a conduit assembly.

FIG. 12 shows a schematic side view of another embodiment of a treatment system 1200 in accordance with aspects of the present technology. The treatment system 1200 can include several features that are generally similar to those of FIGS. 4-11 described above. However, in the treatment system 1200 shown in FIG. 12, the sheath 430 terminates distally at or adjacent a distal end of the hub 406. Accordingly, the sheath 430 and the conduit 420 can be substantially co-terminal. Meanwhile, the inner liner 440 can extend distally beyond the hub 406 and beyond the distal ends of the conduit 420 and sheath 430. Accordingly, in this configuration, the lumen 404 is defined along its entire length by the inner surface of the liner 440. Following severance of the conduit 420 at the detachment zone 426, the liner 440 can be proximally retracted along with the conduit proximal portion 422 and the sheath proximal portion 432. As such, following this proximal retraction, there remains no tubular member extending into an interior of the occlusive member 102. This arrangement may be beneficial if it is desirable to remove any tubular element from within the sac of the aneurysm following deployment of the occlusive member 102 and any embolic element(s).

Figure 13A:
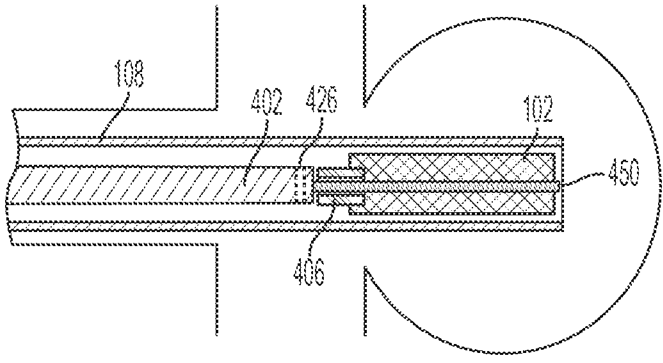
FIGS. 13A-13C illustrate delivery of an occlusive member and embolic element to a treatment site in accordance with aspects of the present technology.
Figure 13B:
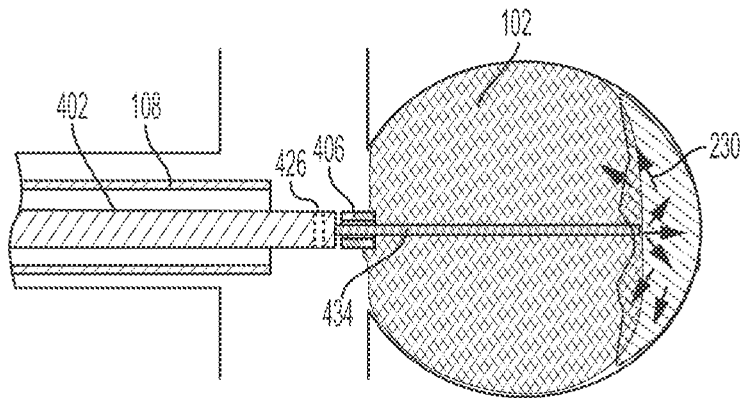
Figure 13C:
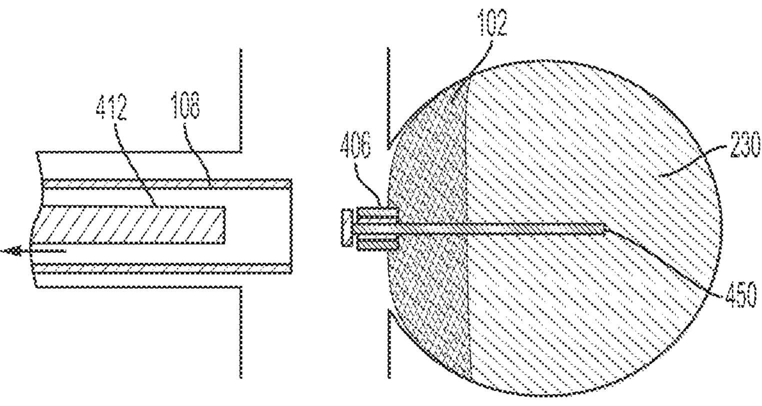

FIGS. 13A-13C illustrate delivery of an occlusive member 102 and embolic element 230 to a treatment site within an aneurysm sac. As shown in FIG. 13A, the treatment system 400 can be positioned within a second elongate shaft 108 (e.g., a microcatheter) for intravascular advancement until the microcatheter is at or adjacent to the aneurysm sac. In the illustrated embodiment, the distal end of the second elongate shaft 108 extends within the aneurysm sac, however in other embodiments the distal end of the second elongate shaft 108 can be positioned at the neck of the aneurysm or proximal to the neck of the aneurysm.

In the position shown in FIG. 13A, the system 400 has been advanced within the elongate shaft 108 such that the occlusive member 102 remains in a constrained, low-profile configuration within the shaft 108 while at least a portion of the conduit assembly 402 extends adjacent to the occlusive member 102 and within the shaft 108. In various embodiments, the shaft 108 can have an inner diameter of about 0.017 inches or less, about 0.021 inches or less, or about 0.027 inches or less.

As shown in FIG. 13B, once the distal opening 450 of the conduit assembly 402 is positioned at or near the treatment site (e.g., within the aneurysm sac), the elongate shaft 108 can be retracted, thereby deploying the occlusive member 102 within the aneurysm sac (e.g., allowing the occlusive member 102 to self-expand). In this position, the embolic element 230 can be advanced through the conduit assembly 402 and into the aneurysm to a region distal to the occlusive member 102. In the case of a fluid or gel, a syringe or other injector may be used to urge the embolic element 230 through the lumen 404. In the case of microcoils or other structural embolic element(s), a delivery wire or other suitable mechanism may be slidably advanced through the lumen 404 of the conduit assembly 402 to position the embolic element 230 into the aneurysm sac.

As described previously with respect to FIGS. 3A-3G, introduction of the embolic element 230 can cause the occlusive member 102 to deform, for example to at least partially fold in on itself to provide for increased protection in a neck region of the aneurysm. Once the embolic element 230 been delivered and the occlusive member 102 has deformed, the occlusive member 102 can be severed from the conduit assembly 402 as described above. For example, a power supply or other current source can be used to generate current through the conduit 420, resulting in electrolytic corrosion of the conduit 420 at the detachment zone 426.

As shown in FIG. 13C, after the occlusive member 102 is released via electrolytic corrosion of the detachment zone 426, the conduit assembly 402 can be proximally retracted while the occlusive member 102 and the embolic element 230 remain positioned within the aneurysm. As the conduit assembly 402 is retracted, the distal portion of the conduit assembly (e.g., the distal portion 434 of the sheath 430 and/or the distal portion 424 of the conduit 420) can remain within the aneurysm and coupled to the occlusive member 102.

IV. Conclusion

Although many of the embodiments are described above with respect to systems and methods related to treatment of hemorrhagic stroke, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-13C.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Unless otherwise indicated, all numbers expressing dimensions, percentages, or other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

Moreover, unless the word “or” is expressly limited to mean only a single item exclusive from the other items in reference to a list of two or more items, then the use of “or” in such a list is to be interpreted as including (a) any single item in the list, (b) all of the items in the list, or (c) any combination of the items in the list. Additionally, the term “comprising” is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The disclosed technology is illustrated, for example, according to various examples described below. Various examples of examples of the disclosed technology are described as numbered examples (1, 2, 3, etc.) for convenience. These are provided as examples and do not limit the disclosed technology. It is noted that any of the dependent examples may be combined in any combination, and placed into a respective independent example. The other examples can be presented in a similar manner.

Example 1. A treatment system comprising: a conduit comprising a proximal portion, a distal portion, and a sidewall, wherein the sidewall defines an electrolytically corrodible detachment zone between the proximal portion and the distal portion, wherein the detachment zone defines one or more apertures formed therein and/or defines a reduced wall thickness relative to non-detachment zone portions of the sidewall so that the detachment zone is configured to cause separation of the proximal portion and the distal portion in response to a flow of an electrical current through the detachment zone, and wherein the conduit defines a lumen configured to pass an embolic element therethrough; an expandable occlusive member comprising a proximal hub coupled to the conduit distal portion, wherein the occlusive member is configured to be positioned at an intrasaccular treatment site; and an elongate conductive member slidably disposed within the lumen and comprising a distally located electrode configured to be disposed adjacent the detachment zone.

Example 2. The treatment system of example 1, wherein the conduit and conductive member are configured such that, in the presence of an electrolytic medium between the conduit sidewall and the conductive member, coupling the conduit to a first terminal of a power supply and coupling the elongate conductive member to a second terminal of a power supply causes current to flow between the detachment zone and the electrode.

Example 3. The treatment system of any one of preceding examples, wherein the detachment zone defines a microstructure with lower crystallinity than each of the conduit proximal portion and the conduit distal portion, and wherein the lower crystallinity facilitates electrolytic severance of the detachment zone.

Example 4. The treatment system of any one of the preceding examples, wherein the detachment zone defines a microstructure that is more amorphous than each of the conduit proximal portion and the conduit distal portion.

Example 5. The treatment system of any one of the preceding examples, wherein the conduit is metallic.

Example 6. The treatment system of any one of the preceding examples, wherein the conduit comprises a hypotube.

Example 7. The treatment system of any one of the preceding examples, wherein the conduit comprises a catheter.

Example 8. The treatment system of any one of the preceding examples, wherein the conduit has a wall thickness of between about 0.0001 inches and about 0.0015 inches.

Example 9. The treatment system of any one of the preceding examples, wherein the conduit has an outer diameter of less than about 0.027 inches, less than about 0.021 inches, less than about 0.017 inches, or less than about 0.015 inches.

Example 10. The treatment system of any one of the preceding examples, wherein the conduit has an inner diameter of less than about 0.020 inches, less than about 0.015 inches, less than about 0.012 inches, less than about 0.010 inches, or less than about 0.008 inches.

Example 11. The treatment system of any one of the preceding examples, further comprising an elongate tubular liner having a second lumen configured to pass an embolic element therethrough.

Example 12. The treatment system of example 11, wherein the liner is configured to be slidably retracted in a proximal direction with respect to the occlusive member following severance of the detachment zone.

Example 13. The treatment system of any one of examples 11-12, wherein the liner is electrically insulative such that electrical current passing through the conduit does not pass through the liner.

Example 14. The treatment system of any one of examples 11-13, wherein the liner comprises a polymer.

Example 15. The treatment system of any one of examples 11-14, wherein the liner comprises polytetrafluoroethylene (PTFE).

Example 16. The treatment system of any one of examples 11-15, wherein the liner defines a gap between a proximal portion and a distal portion that is configured to permit electrical current to flow therethrough, and wherein the gap is axially offset with respect to the detachment zone.

Example 17. The treatment system of any one of examples 11-16, wherein the liner comprises a gap between a proximal portion and a distal portion that is configured to permit electrical current to flow therethrough, and wherein the gap is axially aligned with the detachment zone.

Example 18. The treatment system of any one of any one of the preceding examples, further comprising a sheath extending over the conduit, wherein the sheath is electrically insulative such that electrical current passing through the conduit does not pass through the sheath.

Example 19. The treatment system of example 18, wherein the sheath comprises a polymer.

Example 20. The treatment system of any one of examples 18-19, wherein the sheath comprises polytetrafluoroethylene (PTFE).

Example 21. The treatment system of any one of examples 18-20, wherein the sheath defines a gap between the proximal portion and the distal portion that is configured to permit electrical current to flow therethrough.

Example 22. The treatment system of example 21, wherein the gap between the sheath proximal portion and the sheath distal portion is axially aligned with the detachment zone to permit electrical current to flow between the electrode and the detachment zone.

Example 23. The treatment system of example 21, wherein the gap between the sheath proximal portion and the sheath distal portion is axially offset with respect to the detachment zone while permitting electrical current to flow between the electrode and the detachment zone.

Example 24. The treatment system of any of examples 18-23, wherein the sheath proximal portion is configured to be proximally retracted with respect to the occlusive member following severance of the conduit at the detachment zone.

Example 25. The treatment system of any one of the preceding examples, wherein the electrode comprises a portion of the elongate conductive member that is uninsulated.

Example 26. The treatment system of any one of the preceding examples, wherein the elongate conductive member comprises a shaft portion having a first cross-sectional dimension, and the electrode comprises a portion of the elongate conductive member having a second cross-sectional dimension greater than the first cross-sectional dimension.

Example 27. The treatment system of any one of the preceding examples, wherein the electrode comprises an atraumatic distal face.

Example 28. The treatment system of any one of the preceding examples, wherein the electrode has an outer dimension that tapers in the distal direction to define an atraumatic distal face.

Example 29. The treatment system of any one of the preceding examples, wherein the electrode comprises a ball-shaped element defining an atraumatic distal face.

Example 30. The treatment system of any one of the preceding examples, wherein the elongate conductive member comprises a wire and the electrode comprises a ball disposed at a distal end portion of the wire.

Example 31. The treatment system of any one of the preceding examples, further comprising a plug element disposed proximal to the electrode, the plug element defining a cross-sectional dimension that is substantially the same size as an inner cross-sectional dimension of the lumen.

Example 32. The treatment system of example 31, wherein the plug defines an outer cross-sectional dimension that tapers in the proximal direction.

Example 33. The treatment system of example 31 or example 32, wherein the plug is electrically insulated.

Example 34. The treatment system of any one of the preceding examples, wherein the apertures in the conduit are substantially circular.

Example 35. The treatment system of example 39, wherein the apertures define a diameter, and wherein the apertures are spaced apart from one another with a center-to-center spacing of between 2-4 diameters.

Example 36. The treatment system of any one of the preceding examples, wherein the apertures comprise at least 10, 11, 12, 13, 14, 15, 16, 17, 18, 19, 20, 21, 22, 23, 24, or more apertures.

Example 37. The treatment system of any one of the preceding examples, wherein the conduit is covered with an insulative material along its length, with the detachment zone being at least partially uncovered by insulative material.

Example 38. The treatment system of any one of the preceding examples, wherein the elongate conductive member is covered with insulative material along its length, with the electrode being not covered with insulative material.

Example 39. The treatment system of any one of the preceding examples, further comprising a microcatheter defining a second lumen configured to slidably receive the conduit therethrough.

Example 40. The treatment system of any one of the preceding examples, wherein the embolic element comprises one or more of: a coil or a liquid embolic.

Example 41. The treatment system of any one of the preceding examples, wherein the occlusive member comprises an expandable medical device.

Example 42. The treatment system of any one of the preceding examples, wherein the occlusive member comprises a self-expandable mesh.

Example 43. A treatment system comprising: an elongate tubular member comprising: a proximal portion, a distal portion, and a sidewall, wherein the sidewall defines an electrolytically corrodible detachment zone between the proximal portion and the distal portion, wherein the detachment zone defines one or more apertures formed therein and/or defines a reduced wall thickness relative to non-detachment zone portions of the sidewall; and a lumen extending therethrough; a medical device coupled to the tubular member distal portion; and an elongate rod slidably disposed within the tubular member lumen and having a distally located electrode configured to be disposed adjacent the detachment zone.

Example 44. The treatment system of example 43, wherein the medical device comprises an occlusive member.

Example 45. The treatment system of example 43 or example 44, wherein the medical device is configured to be deployed within an aneurysm.

Example 46. The treatment system of any one of examples 43-45, wherein the tubular member and rod are configured such that when, while in the presence of an electrolytic medium, the tubular member is coupled to a first terminal of a power supply and the elongate rod member is coupled to a second terminal of a power supply, current flows between the detachment zone and the electrode.

Example 47. The treatment system of any one of examples 43-46, wherein the detachment zone comprises a portion of the tubular member configured to be severed in response to delivery of electrical current thereto.

Example 48. The treatment system of any one of examples 43-47, wherein the detachment zone has a microstructure with lower crystallinity than each of the tubular member proximal portion and the tubular member distal portion.

Example 49. The treatment system of any one of examples 43-48, wherein the detachment zone has a microstructure that is more amorphous than each of the tubular member proximal portion and the tubular member distal portion.

Example 50. The treatment system of any one of examples 43-49, wherein the tubular member is metallic.

Example 51. The treatment system of any one of examples 43-50, wherein the tubular member comprises a hypotube.

Example 52. The treatment system of any one of examples 43-51, wherein the tubular member comprises a catheter.

Example 53. The treatment system of any one of examples 43-52, wherein the tubular member has a wall thickness of between about 0.0005 inches and about 0.0015 inches.

Example 54. The treatment system of any one of examples 43-53, wherein the tubular member has an outer diameter of less than about 0.027 inches, less than about 0.021 inches, less than about 0.017 inches, or less than about 0.015 inches.

Example 55. The treatment system of any one of examples 43-54, wherein the tubular member has an inner diameter of less than about 0.015 inches, less than about 0.012 inches, less than about 0.010 inches, or less than about 0.008 inches.

Example 56. The treatment system of any one of examples 43-55, further comprising a liner extending through the tubular member lumen.

Example 57. The treatment system of example 56, wherein the liner comprises an elongate tubular member having a second lumen configured to pass an embolic element therethrough.

Example 58. The treatment system of example 56 or example 57, wherein the liner is configured to be slidably retracted with respect to the occlusive member following severance of the detachment zone.

Example 59. The treatment system of any one of the examples 56-58, wherein the liner is electrically insulative.

Example 60. The treatment system of any one of examples 56-59, wherein the liner comprises a polymer.

Example 61. The treatment system of any one of examples 56-60, wherein the liner comprises polytetrafluoroethylene (PTFE).

Example 62. The treatment system of any one of examples 56-61, wherein the liner comprises a gap between a proximal portion and a distal portion, and wherein the gap is axially offset with respect to the detachment zone.

Example 63. The treatment system of any one of examples 56-62, wherein the liner comprises a gap between a proximal portion and a distal portion, and wherein the gap is axially aligned with the detachment zone.

Example 64. The treatment system of any one of examples 43-63, further comprising a sheath extending over the tubular member.

Example 65. The treatment system of example 64, wherein the sheath is electrically insulative.

Example 66. The treatment system of example 64 or example 65, wherein the sheath comprises a polymer.

Example 67. The treatment system of any one of examples 64-66, wherein the sheath comprises polytetrafluoroethylene (PTFE).

Example 68. The treatment system of any one of examples 64-67, wherein the sheath comprises a gap between the proximal portion and the distal portion.

Example 69. The treatment system of example 68, wherein the gap between the sheath proximal portion and the sheath distal portion is axially aligned with the detachment zone.

Example 70. The treatment system of example 69, wherein the gap between the sheath proximal portion and the sheath distal portion is axially offset with respect to the detachment zone.

Example 71. The treatment system of any of examples 64-70, wherein the sheath proximal portion is configured to be proximally retracted with respect to the occlusive member following severance of the tubular member at the detachment zone.

Example 72. The treatment system of any one of examples 43-71, wherein the electrode comprises a portion of the elongate rod that is uninsulated.

Example 73. The treatment system of any one of examples 43-72, wherein the electrode comprises a portion of the elongate rod that has an enlarged cross-sectional dimension.

Example 74. The treatment system of any one of examples 43-73, wherein the electrode comprises an atraumatic distal face.

Example 75. The treatment system of any one of examples 43-74, wherein the electrode has an outer dimension that tapers in the distal direction.

Example 76. The treatment system of any one of examples 43-75, wherein the electrode comprises a ball-shaped element.

Example 77. The treatment system of any one of examples 43-76, wherein the elongate rod comprises a wire and the electrode comprises a ball disposed at a distal end portion of the wire.

Example 78. The treatment system of any one of examples 43-77, further comprising a plug element disposed proximal to the electrode, the plug element having a cross-sectional dimension that is substantially the same size an inner cross-sectional dimension of the lumen.

Example 79. The treatment system of example 78, wherein the plug has an outer cross-sectional dimension that tapers in the proximal direction.

Example 80. The treatment system of example 78 or example 79, wherein the plug is electrically insulated.

Example 81. The treatment system of any one of examples 43-80, wherein the apertures in the tubular member are substantially circular.

Example 82. The treatment system of example 81, wherein the apertures have a diameter, and wherein the apertures are spaced apart from one another with a center-to-center spacing of between 1-3 diameters.

Example 83. The treatment system of any one of examples 43-82, wherein the apertures comprise at least 10, 11, 12, 13, 14, 15, 16, 17, 18, 19, 20, 21, 22, 23, 24, or more apertures.

Example 84. The treatment system of any one of examples 43-83, wherein the tubular member is electrically insulated along its length, with the detachment zone being uninsulated.

Example 85. The treatment system of any one of examples 43-84, wherein the elongate rod is covered with insulative material along its length, with the electrode being uninsulated.

Example 86. The treatment system of any one of examples 43-85, further comprising a microcatheter having a second lumen configured to slidably receive the tubular member therethrough.

Example 87. The treatment system of any one of examples 43-86, wherein the embolic element comprises one or more of: a coil or a liquid embolic.

Example 88. The treatment system of any one of examples 43-87, wherein the medical device comprises an expandable medical mesh.

Example 89. The treatment system of any one of examples 43-88, wherein the medical device comprises a self-expandable mesh.

Example 90. A method comprising: disposing an occlusive member at a treatment site, the occlusive member coupled to a distal end of a conduit having a sidewall that defines a detachment zone that includes a one or more apertures formed therein and/or a reduced wall thickness relative to non-detachment zone portions of the sidewall; expanding the occlusive member at the treatment site; disposing an elongate conductive member within a lumen of the conduit such that a distally located electrode is positioned adjacent to the detachment zone; applying a voltage across the conduit and the elongate conductive member, thereby electrolytically severing the conduit at the detachment zone; and proximally retracting both the conduit and the conductive member while the occlusive member remains within the aneurysm cavity.

Example 91. The method of example 90, wherein the treatment site comprises an aneurysm sac.

Example 92. The method of example 91, wherein disposing the occlusive member comprises distally advancing the occlusive member and the conduit through a patient's vasculature to reach the aneurysm sac.

Example 93. The method of any one of examples 90-92, further comprising delivering an embolic element through the conduit to the treatment site.

Example 94. The method of any one of examples 90-93, wherein expanding the occlusive member comprises releasing the occlusive member from a surrounding catheter such that the occlusive member self-expands to assume an expanded state.

Example 95. The method of any one of examples 90-94, wherein the electrode comprises a portion of the elongate conductive member that is uninsulated.

Example 96. The method of any one of examples 90-95, wherein the elongate conductive member comprises a wire and the electrode comprises a ball disposed at a distal end portion of the wire.

Example 97. The method of any one of examples 90-96, wherein the elongate conductive member further comprises a plug element disposed proximal to the electrode, the plug element having a cross-sectional dimension that is substantially the same size as an inner cross-sectional dimension of the lumen.

Example 98. The method of any one of examples 90-97, wherein the conduit is electrically insulated along its length, with the detachment zone being uninsulated.

Example 99. The method of any one of examples 90-98, wherein the elongate conductive member is covered with insulative material along its length, with the electrode being uninsulated.

Example 100. The method of any one of examples 92-99, wherein the embolic element comprises one or more of: a coil or a liquid embolic.

The invention claimed is:

1. A treatment system comprising:

a conduit comprising a proximal portion, a distal portion, and a sidewall, wherein the sidewall defines an electrolytically corrodible detachment zone between the proximal portion and the distal portion, wherein the detachment zone defines one or more apertures formed therein and/or defines a reduced wall thickness relative to non-detachment zone portions of the sidewall so that the detachment zone is configured to cause separation of the proximal portion and the distal portion in response to a flow of an electrical current through the detachment zone, and wherein the conduit defines a lumen configured to pass a liquid embolic element therethrough;

an expandable occlusive member comprising a proximal hub coupled to the conduit distal portion, wherein the occlusive member is configured to be positioned at an intrasaccular treatment site; and an elongate conductive member slidably disposed within the lumen and slidable relative to the expandable occlusive member, the elongate conductive member comprising:

a distally located electrode configured to be disposed adjacent to the detachment zone; and a plug element disposed proximal to the electrode, wherein the elongate conductive member is axially movable relative to the conduit between a first position and a second position, wherein in the first position, the plug element is disposed distal to the detachment zone such that the lumen is configured to pass the liquid embolic element therethrough, and wherein in the second position, the plug element is disposed proximal to the detachment zone such that the plug element substantially occludes the lumen to prevent the liquid embolic element from passing distally beyond the plug element.

2. The treatment system of claim 1, wherein the conduit and conductive member are configured such that, in the presence of an electrolytic medium between the conduit sidewall and the conductive member, coupling the conduit to a first terminal of a power supply and coupling the elongate conductive member to a second terminal of a power supply causes current to flow between the detachment zone and the electrode.

3. The treatment system of claim 1, further comprising an elongate tubular liner having a second lumen configured to pass the liquid embolic element therethrough.

4. The treatment system of claim 3, wherein the liner is electrically insulative such that electrical current passing through the conduit does not pass through the liner, the liner defining a gap between a liner proximal portion and a liner distal portion that is configured to permit electrical current to flow therethrough.

5. The treatment system of claim 1, further comprising a sheath extending over the conduit, wherein the sheath is electrically insulative such that electrical current passing through the conduit does not pass through the sheath, wherein the sheath defines a gap between a sheath proximal portion and a sheath distal portion that is configured to permit electrical current to flow therethrough.

6. The treatment system of claim 1, wherein the elongate conductive member comprises a shaft portion having a first cross-sectional dimension, and the electrode comprises a portion of the elongate conductive member having a second cross-sectional dimension greater than the first cross-sectional dimension.

7. The treatment system of claim 1, wherein the elongate conductive member comprises a wire and the electrode comprises a ball disposed at a distal end portion of the wire.

8. The treatment system of claim 1, wherein the plug element defines a cross-sectional dimension that is substantially the same size as an inner cross-sectional dimension of the lumen.

9. A treatment system comprising:

an elongate tubular member comprising:

a proximal portion, a distal portion, and a sidewall, wherein the sidewall defines an electrolytically corrodible detachment zone between the proximal portion and the distal portion, wherein the detachment zone defines one or more apertures formed therein and/or defines a reduced wall thickness relative to non-detachment zone portions of the sidewall; and a lumen extending therethrough;

a medical device coupled to the tubular member distal portion; and an elongate rod slidably disposed within the tubular member lumen and slidable relative to the medical device, the elongate rod having a distally located electrode configured to be disposed adjacent to the detachment zone and a plug element disposed proximal to the electrode, the plug element having a cross-sectional dimension that is substantially the same size as an inner cross-sectional dimension of the lumen, wherein the elongate rod is axially moveable relative to the medical device between a first position and a second position, wherein in the first position, the plug element is disposed distal to the detachment zone such that the lumen is configured to pass a liquid embolic element therethrough, and wherein in the second position, the plug element is disposed proximal to the detachment zone such that the plug element substantially occludes the lumen to prevent the liquid embolic element from passing distally beyond the plug element.

10. The treatment system of claim 9, wherein the tubular member and rod are configured such that when, while in the presence of an electrolytic medium, the tubular member is coupled to a first terminal of a power supply and the elongate rod is coupled to a second terminal of a power supply, current flows between the detachment zone and the electrode.

11. The treatment system of claim 9, further comprising an electrically insulative liner extending through the tubular member lumen, the liner defining a gap between a liner proximal portion and a liner distal portion.

12. The treatment system of claim 9, further comprising an electrically insulative sheath extending over the tubular member, the sheath defining a gap between a sheath proximal portion and a sheath distal portion.

13. The treatment system of claim 9, wherein the electrode comprises a portion of the elongate rod that has an enlarged cross-sectional dimension.

14. The treatment system of claim 9, wherein the elongate rod comprises a wire and the electrode comprises a ball disposed at a distal end portion of the wire.

15. The treatment system of claim 9, wherein the plug element has an outer cross-sectional dimension that tapers in a proximal direction.

16. A method comprising:

disposing an occlusive member at a treatment site, the occlusive member coupled to a distal end of a conduit having a sidewall that defines a detachment zone that includes one or more apertures formed therein and/or a reduced wall thickness relative to non-detachment zone portions of the sidewall;

expanding the occlusive member at the treatment site;

disposing an elongate conductive member within a lumen of the conduit in a first position such that a distally located electrode and a plug element disposed proximal to the electrode are positioned distal to the detachment zone;

delivering a liquid embolic element through the lumen of the conduit to the treatment site while the elongate conductive member is in the first position;

moving the elongate conductive member proximally relative to the conduit to a second position such that the electrode is positioned adjacent to the detachment zone and the plug element is substantially occludes the lumen;

applying a voltage across the conduit and the elongate conductive member while the elongate conductive member is in the second position, thereby electrolytically severing the conduit at the detachment zone; and proximally retracting both the conduit and the conductive member while the occlusive member remains at the treatment site.

17. The method of claim 16, wherein the treatment site comprises an aneurysm sac.

18. The method of claim 16, wherein the elongate conductive member comprises a wire and the electrode comprises a ball disposed at a distal end portion of the wire.

19. The method of claim 16, wherein the plug element defines a cross-sectional dimension that is substantially the same size as an inner cross-sectional dimension of the lumen.

* * * * *